US012642864B2

(12) United States Patent
Wells et al.

(10) Patent No.: US 12,642,864 B2
(45) Date of Patent: Jun. 2, 2026

(54) METHIONINE CONTAINING ANTIBODIES FOR CONJUGATION OF AGENTS

(71) Applicant: The Regents of the University of California, Oakland, CA (US)

(72) Inventors: James Wells, San Francisco, CA (US); Hai Tran, San Francisco, CA (US); Susanna Elledge, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1288 days.

(21) Appl. No.: 17/419,246

(22) PCT Filed: Dec. 30, 2019

(86) PCT No.: PCT/US2019/068985

§ 371 (c)(1),
(2) Date: Jun. 28, 2021

(87) PCT Pub. No.: WO2020/140123

PCT Pub. Date: Jul. 2, 2020

(65) Prior Publication Data

US 2022/0072148 A1 Mar. 10, 2022

Related U.S. Application Data

(60) Provisional application No. 62/891,249, filed on Aug. 23, 2019, provisional application No. 62/786,331, filed on Dec. 28, 2018.

(51) Int. Cl.

| | |
|---|---|
| ***A61K 47/68*** | (2017.01) |
| ***A61K 39/00*** | (2006.01) |
| ***C07D 413/06*** | (2006.01) |
| ***C07K 16/32*** | (2006.01) |
| ***C07K 16/46*** | (2006.01) |

(52) U.S. Cl.

CPC ...... *A61K 47/6889* (2017.08); *A61K 47/6803* (2017.08); *A61K 47/68031* (2023.08); *A61K 47/6851* (2017.08); *A61K 47/6855* (2017.08); *C07D 413/06* (2013.01); *C07K 16/32* (2013.01); *C07K 16/464* (2013.01); *A61K 2039/505* (2013.01); *C07K 2317/55* (2013.01); *C07K 2317/92* (2013.01)

(58) Field of Classification Search

CPC ........... A61K 47/6889; A61K 47/6803; A61K 47/68031; A61K 47/6851; A61K 47/6855; A61K 2039/505; A61K 47/6849; C07D 413/06; C07K 16/32; C07K 16/464; C07K 2317/55; C07K 2317/92; C07K 2317/24; C07K 2317/52; C07K 2317/94

See application file for complete search history.

(56) References Cited

U.S. PATENT DOCUMENTS

2011/0301334 A1* 12/2011 Bhakta .................... A61P 17/04
530/391.1

FOREIGN PATENT DOCUMENTS

| | | | | |
|---|---|---|---|---|
| AU | 2014200636 A1 * | 2/2014 | ........... | A61K 39/395 |
| WO | WO-2017127791 A1 * | 7/2017 | ........... | C07D 213/79 |
| WO | WO-2018089951 A1 * | 5/2018 | ........... | A61K 47/643 |
| WO | WO-2020036904 A1 * | 2/2020 | ........... | C07D 273/00 |

OTHER PUBLICATIONS

Sela-Culang, et al., Front. In Immunol. 2013; vol. 4 Article 302 (Year: 2013).*

Lin, S. et al., ‘Redox-based reagents for chemoselective methionine bioconjugation’, Science, Feb. 10, 2017, vol. 355, pp. 597-602; see abstract; pp. 1, 3, 6; and figure 2.

Taylor, M. T. et al., ‘A protein functionalization platform based on selective reactions at methionine residues’, Nature, Oct. 25, 2018, vol. 562, pp. 563-568 see:abstract; and p. 563.

Wang, C. et al., ‘Mechanism and Origin of Chemical Selectivity in Oxaziridine-Based Methionine Modification: A Computational Study’, The Journal of Organic Chemistry, 2017, vol. 82, pp. 9765-9772 see the whole document.

Williamson, K. S. et al., ‘Advances in the Chemistry of Oxaziridines’, Chemical Reviews, 2014, vol. 114, pp. 8016-8036 See the whole document.

* cited by examiner

*Primary Examiner* — Julie Wu
*Assistant Examiner* — Sydney Van Druff
(74) *Attorney, Agent, or Firm* — MARSHALL, GERSTEIN, AND BORUN, LLP

(57) ABSTRACT

Provided herein are novel antibody-agent conjugates formed by the introduction of methionine residues to antibody scaffold light or heavy chains at select positions, followed by conjugation of the agent to the methionine, for example, by oxaziridine chemistries. Methionine substitutions at the targeted positions enable highly efficient functionalization to form very stable conjugates, including conjugates suitable for in vivo use. The positions were identified for the trastuzumab and other related scaffolds which can be engineered for affinity to any target antigen. The conjugates include ADCs and detections agents. Also disclosed are novel oxaziridine reagents for conjugation to methionines in proteins.

21 Claims, 3 Drawing Sheets

Specification includes a Sequence Listing.

SEQUENCE LISTING

```
<160> NUMBER OF SEQ ID NOS: 10

<210> SEQ ID NO 1
<211> LENGTH: 214
```

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ala Ser Gln Asp Val Asn Thr Ala Val Ala
1               5                   10


<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ala Ser Phe Leu Tyr Ser
1               5
```

-continued

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

```
Gln Gln His Tyr Thr Thr Pro Pro Thr
1               5
```

<210> SEQ ID NO 5
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

-continued

```
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Asn Ile Lys Asp Thr Tyr Ile His
1               5                   10


<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ile Tyr Pro Thr Asn Gly Tyr Thr Arg Tyr Ala Asp Ser Val Lys
1               5                   10                  15

Gly


<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Gly Gly Asp Gly Phe Tyr Ala Met Asp Tyr
1               5                   10


<210> SEQ ID NO 9
<211> LENGTH: 187
```

-continued

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Arg
        35                  40                  45

Ser Gly Thr Asp Phe Thr Leu Thr Ile Ser Ser Leu Gln Pro Glu Asp
    50                  55                  60

Phe Ala Thr Tyr Tyr Cys Phe Gly Gln Gly Thr Lys Val Glu Ile Lys
65                  70                  75                  80

Arg Thr Val Ala Ala Pro Ser Val Phe Ile Phe Pro Pro Ser Asp Glu
                85                  90                  95

Gln Leu Lys Ser Gly Thr Ala Ser Val Val Cys Leu Leu Asn Asn Phe
            100                 105                 110

Tyr Pro Arg Glu Ala Lys Val Gln Trp Lys Val Asp Asn Ala Leu Gln
        115                 120                 125

Ser Gly Asn Ser Gln Glu Ser Val Thr Glu Gln Asp Ser Lys Asp Ser
    130                 135                 140

Thr Tyr Ser Leu Ser Ser Thr Leu Thr Leu Ser Lys Ala Asp Tyr Glu
145                 150                 155                 160

Lys His Lys Val Tyr Ala Cys Glu Val Thr His Gln Gly Leu Ser Ser
                165                 170                 175

Pro Val Thr Lys Ser Phe Asn Arg Gly Glu Cys
            180                 185
```

<210> SEQ ID NO 10
<211> LENGTH: 412
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Ala Arg Phe Thr Ile Ser Ala Asp Thr Ser
        35                  40                  45

Lys Asn Thr Ala Tyr Leu Gln Met Asn Ser Leu Arg Ala Glu Asp Thr
    50                  55                  60

Ala Val Tyr Tyr Cys Ser Arg Trp Gly Gln Gly Thr Leu Val Thr Val
65                  70                  75                  80

Ser Ser Ala Ser Thr Lys Gly Pro Ser Val Phe Pro Leu Ala Pro Ser
                85                  90                  95

Ser Lys Ser Thr Ser Gly Gly Thr Ala Ala Leu Gly Cys Leu Val Lys
            100                 105                 110

Asp Tyr Phe Pro Glu Pro Val Thr Val Ser Trp Asn Ser Gly Ala Leu
        115                 120                 125
```

-continued

| | | | | | | | | | | | | | | | |
|---|---|---|---|---|---|---|---|---|---|---|---|---|---|---|---|
| Thr | Ser | Gly | Val | His | Thr | Phe | Pro | Ala | Val | Leu | Gln | Ser | Ser | Gly | Leu |
| | 130 | | | | | 135 | | | | | 140 | | | | |
| Tyr | Ser | Leu | Ser | Ser | Val | Val | Thr | Val | Pro | Ser | Ser | Ser | Leu | Gly | Thr |
| 145 | | | | | 150 | | | | | 155 | | | | | 160 |
| Gln | Thr | Tyr | Ile | Cys | Asn | Val | Asn | His | Lys | Pro | Ser | Asn | Thr | Lys | Val |
| | | | | 165 | | | | | 170 | | | | | 175 | |
| Asp | Lys | Lys | Val | Glu | Pro | Lys | Ser | Cys | Asp | Lys | Thr | His | Thr | Cys | Pro |
| | | | 180 | | | | | 185 | | | | | 190 | | |
| Pro | Cys | Pro | Ala | Pro | Glu | Leu | Leu | Gly | Gly | Pro | Ser | Val | Phe | Leu | Phe |
| | | 195 | | | | | 200 | | | | | 205 | | | |
| Pro | Pro | Lys | Pro | Lys | Asp | Thr | Leu | Met | Ile | Ser | Arg | Thr | Pro | Glu | Val |
| | 210 | | | | | 215 | | | | | 220 | | | | |
| Thr | Cys | Val | Val | Val | Asp | Val | Ser | His | Glu | Asp | Pro | Glu | Val | Lys | Phe |
| 225 | | | | | 230 | | | | | 235 | | | | | 240 |
| Asn | Trp | Tyr | Val | Asp | Gly | Val | Glu | Val | His | Asn | Ala | Lys | Thr | Lys | Pro |
| | | | | 245 | | | | | 250 | | | | | 255 | |
| Arg | Glu | Glu | Gln | Tyr | Asn | Ser | Thr | Tyr | Arg | Val | Val | Ser | Val | Leu | Thr |
| | | | 260 | | | | | 265 | | | | | 270 | | |
| Val | Leu | His | Gln | Asp | Trp | Leu | Asn | Gly | Lys | Glu | Tyr | Lys | Cys | Lys | Val |
| | | 275 | | | | | 280 | | | | | 285 | | | |
| Ser | Asn | Lys | Ala | Leu | Pro | Ala | Pro | Ile | Glu | Lys | Thr | Ile | Ser | Lys | Ala |
| | 290 | | | | | 295 | | | | | 300 | | | | |
| Lys | Gly | Gln | Pro | Arg | Glu | Pro | Gln | Val | Tyr | Thr | Leu | Pro | Pro | Ser | Arg |
| 305 | | | | | 310 | | | | | 315 | | | | | 320 |
| Glu | Glu | Met | Thr | Lys | Asn | Gln | Val | Ser | Leu | Thr | Cys | Leu | Val | Lys | Gly |
| | | | | 325 | | | | | 330 | | | | | 335 | |
| Phe | Tyr | Pro | Ser | Asp | Ile | Ala | Val | Glu | Trp | Glu | Ser | Asn | Gly | Gln | Pro |
| | | | 340 | | | | | 345 | | | | | 350 | | |
| Glu | Asn | Asn | Tyr | Lys | Thr | Thr | Pro | Pro | Val | Leu | Asp | Ser | Asp | Gly | Ser |
| | | 355 | | | | | 360 | | | | | 365 | | | |
| Phe | Phe | Leu | Tyr | Ser | Lys | Leu | Thr | Val | Asp | Lys | Ser | Arg | Trp | Gln | Gln |
| | 370 | | | | | 375 | | | | | 380 | | | | |
| Gly | Asn | Val | Phe | Ser | Cys | Ser | Val | Met | His | Glu | Ala | Leu | His | Asn | His |
| 385 | | | | | 390 | | | | | 395 | | | | | 400 |
| Tyr | Thr | Gln | Lys | Ser | Leu | Ser | Leu | Ser | Pro | Gly | Lys | | | | |
| | | | | 405 | | | | | 410 | | | | | | |

METHIONINE CONTAINING ANTIBODIES FOR CONJUGATION OF AGENTS

CROSS-REFERENCE TO RELATED APPLICATIONS

This application is a 35 USC § 371 national stage application of PCT international patent application number PCT/US2019/068985, entitled "Novel Methionine Containing Antibodies for Conjugation of Agents," filed Dec. 30, 2019, which claims the benefit of priority to U.S. Provisional Application Ser. No. 62/786,331 entitled "Novel Methionine Containing Antibodies for Conjugation of Agents," filed Dec. 28, 2018, and U.S. Provisional Application Ser. No. 62/891,249 entitled "Novel Methionine Containing Antibodies for Conjugation of Agents," filed Aug. 23, 2019, the contents of these applications being hereby incorporated by reference.

STATEMENT REGARDING FEDERALLY SPONSORED RESEARCH OR DEVELOPMENT

This invention was made with government support under grants no. P41 CA196276 and R21 AI111662 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 27, 2019, is named UCSF073PCT_SL.txt and is 13,136 bytes in size.

BACKGROUND OF THE INVENTION

Chemical modification of antibodies is one of the most important bioconjugations utilized by biologists and biotechnology. Chemical bioconjugation has been instrumental in expanding the utility of monoclonal antibodies, both as probes and therapeutics, by facilitating covalent attachment of a variety of moieties such as fluorophores, or cytotoxic agents in the form of antibody drug conjugates (ADCs).

To date, methods of antibody conjugation has largely been achieved by random modification of lysines, by functionalized N-hydroxy succinamides. However, antibodies typically have about 40 surface exposed lysine residues per IgG which can result in more than one million different lysine-conjugated species from a single conjugation reaction. These conjugates are therefore highly heterogenous in terms of conjugation site and drug-to-antibody-ratio. The conjugated cytotoxic drugs tend to be hydrophobic causing aggregation, immunogenicity, faster clearance rates and thus differences in the pharmacodynamic properties of the conjugate. Additionally, the specific site of conjugation can have an effect on the efficacy of the ADC based on the stability and the aggregation propensity of the resulting derivative.

Meanwhile, cysteine is far less abundant than lysine and affords greater site-selectivity. Selective mutagenesis of antibodies to introduce cysteine residues enables conjugation by maleimides to form stable thioether linkages. Cysteine modification potentially enables site-specific modification of antibodies and more control over the consistency of end products, for example, as described in United States Patent Application Publication Number US20110301334, entitled "Cysteine Engineered Antibodies and Conjugates," by Bhakta and Junutula. However, typical cysteine modification approaches usually require reducing the interchain disulfide bonds of the antibody and re-conjugating to a thiol reactive moiety, either resulting in disrupted disulfide bonds or re-bridged disulfides. Additionally, the reduction process can cause disulfide scrambling which can disrupt the stability and even the structure of the antibody by forming different disulfide connections.

Accordingly, there is a need in the art for improved protein and antibody conjugation chemistries that are efficient, produce stable conjugations, are site-selective for homogeneity/reproducibility, and which do not impair the overall functional properties of the protein.

The use of introduced methionines has been proposed for the selective formation of conjugates. Recently, a methionine specific chemistry has been developed, redox-activated chemical tagging (ReACT), to efficiently and site-specifically conjugate to methionine residues on proteins. The ReACT methionine chemistry involves oxidation of methionine to form a sulfimide adduct with an oxaziridine molecule functionalized with an alkyl-azide to allow cargo attachment via click chemistry. Other methionine modification methodologies are known in the art, including, for example, in PCT Patent Application Publication Number WO/2018089951, entitled "Redox-Based Reagents for Methionine Bioconjugation," by Chang et al., novel chemistries are disclosed for stable conjugation of agents to antibodies to methionine.

However, as is known from cysteine modification and other studies, the location of the modified residue in the antibody chain sequences will strongly affect the conjugation efficiency, conjugate stability, and binding activity of the antibody. Accordingly, in order for methionine-based conjugation methods to be successfully applied, the site of methionine introduction must be targeted to positions that produce stable conjugates with high efficiency. Accordingly, there is a need in the art for novel methionine substituted antibodies, and conjugates thereof, having properly targeted methionine substitutions.

SUMMARY OF THE INVENTION

As described herein, the inventors of the present disclosure have, by extensive experimentation, discovered antibody light and heavy chain positions in a widely used antibody scaffold that are amenable to methionine substitution, followed by conjugation of agents with high labeling yields and the formation of stable conjugates, including conjugated compositions suitable for in vivo use. The various embodiments of the invention thus provide the art with novel antibodies, antibody-agent conjugates, and associated methods for therapeutic and diagnostic applications.

In a first aspect, the scope of the invention encompasses functionalized antigen-binding polypeptides. The polypeptides of the invention comprise antibodies, antibody-binding fragments based thereon, and other derivatives thereof. These antigen-binding proteins are functionalized with one or more agents, the functionalization occurring by conjugation to introduced methionine residues, for example by oxaziridine chemistry. The methionine residues are introduced at select positions which were discovered to result in efficient conjugation, high yields in expression systems, and the formation of highly stable conjugates, for example, suitable for in vivo use, while maintaining high affinity for target antigens.

In another aspect, the scope of the invention encompasses particular classes of methionine-linked conjugates, including detection agents and therapeutic agents, such as cytotoxic payloads and ADCs. The scope of the invention also encompasses methods of using the functionalized antigen binding compositions of the invention, as in detection methods and therapeutic applications.

In another aspect, the scope of the invention further encompasses nucleic acids and transformed cells which code for and express the methionine-substituted antibody chains comprising substitutions at sites disclosed herein.

The scope of the invention further encompasses methods of functionalizing methionine residues present in antibodies and other polypeptides, by the identification of certain oxaziridine conjugation agents that are highly effective for the formation of stable conjugates.

BRIEF DESCRIPTION OF THE DRAWINGS

FIG. 1A depicts the general scheme of modular oxaziridine labeling on trastuzumab Fab. After conjugation with oxaziridine, different functionalities can be conjugated by click chemistry. FIG. 1B depicts the synthesis of oxaziridine composition #16.

FIG. 2. depicts the stability of oxaziridines conjugated to a GFP binding Fab based on the trastuzumab scaffold at site LC.T20M over 3 days at 37° C. for each derivative (n=3) produced using the oxaziridine compositions of Table 1. Oxaziridine 6 is not shown because it showed 0% stability. Oxaziridine 10 is not shown because no initial labeling could be detected.

FIG. 3 depicts the stability of oxaziridine compound #16 conjugated to a GFP binding Fab based on the trastuzumab scaffold at 14 selected methionine substitution sites after incubation at 37° C. for 3 days (n=3). The dotted line indicates 85% stability.

DESCRIPTION OF THE INVENTION

Figure 1A:
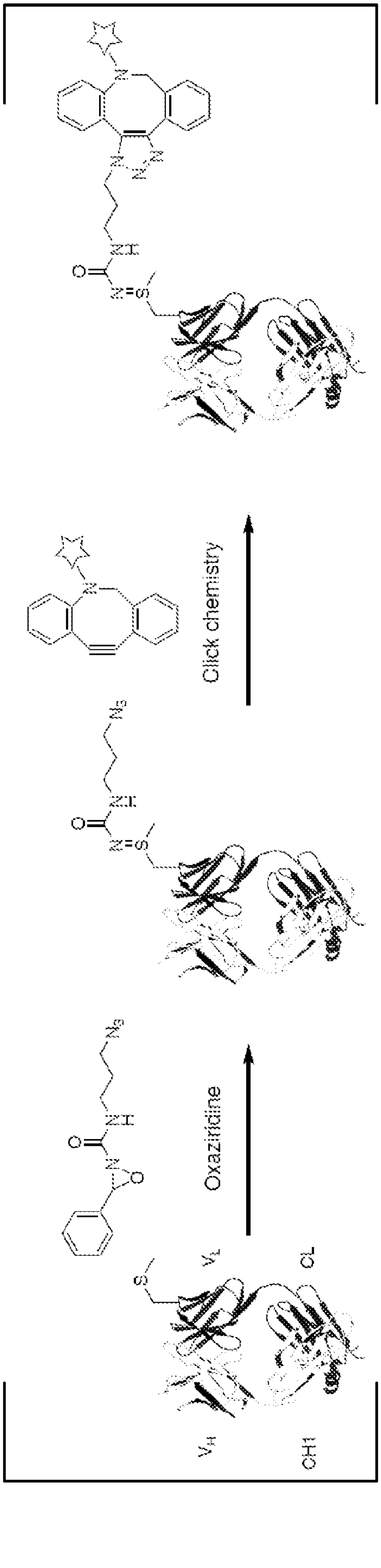
FIGS. 1A and 1B.
Figure 1B:
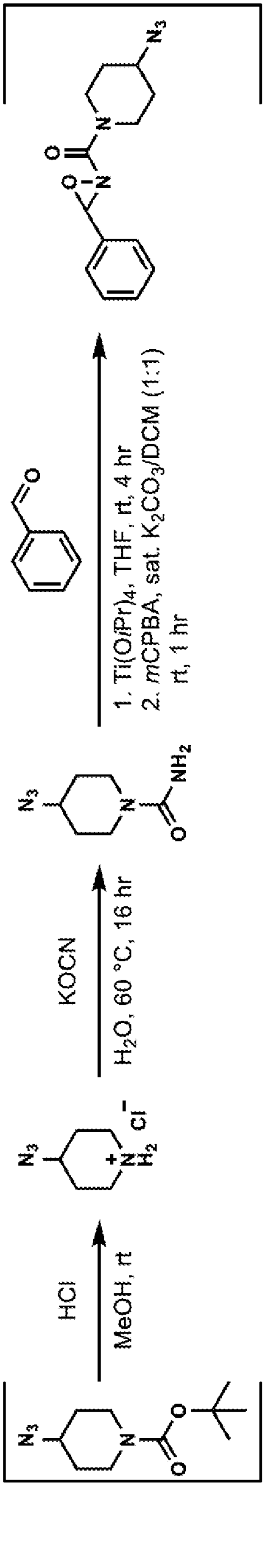
Figure 2:
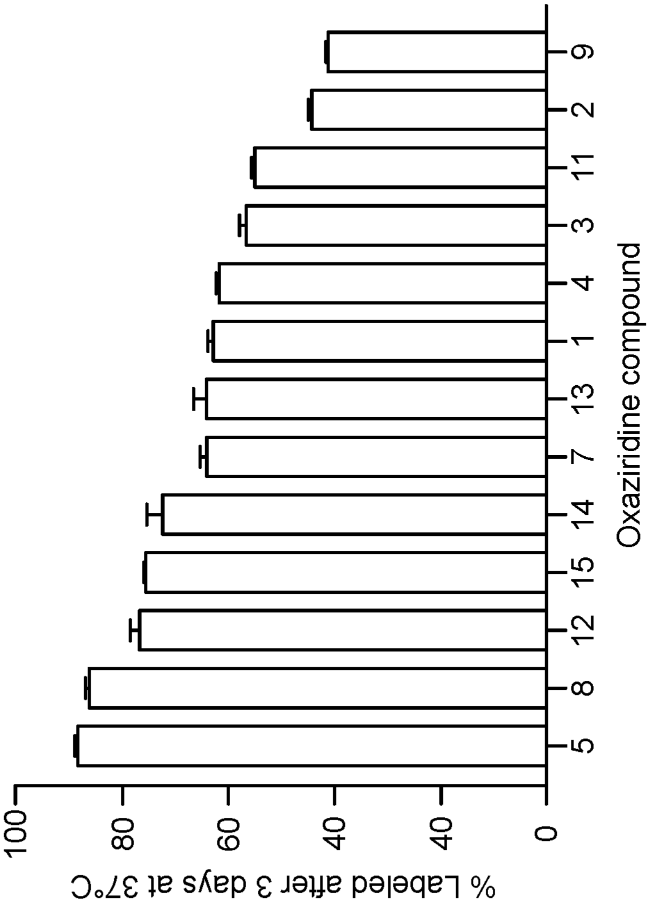
FIG. 2.
Figure 3:
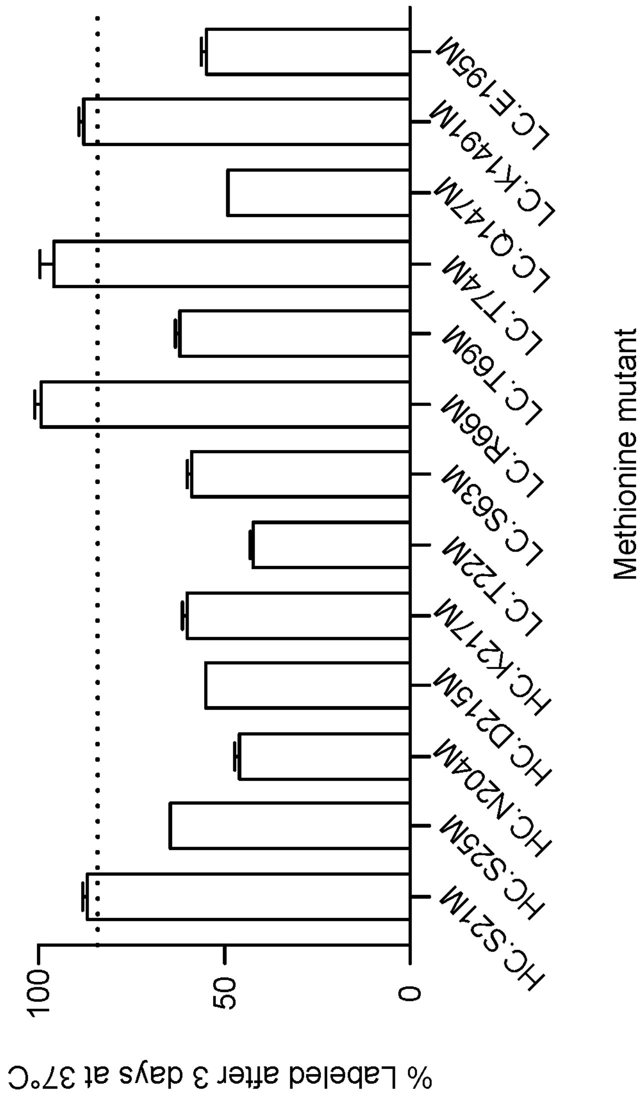
FIG. 3.

Definitions. The various inventions disclosed herein are directed to antigen binding compositions comprising antibodies and antibody fragments wherein introduced methionines are utilized as reactive handles for functionalization with active agents. Disclosed herein are novel methods of conjugation, as well as numerous methionine conjugation sites wherein stable conjugations may be made with high efficiency. The following definitions will aid in an understanding of the various embodiments of the invention disclosed herein.

Antigen binding composition. As used herein, an "antigen binding composition" is a composition of the invention which selectively binds to a target antigen with high affinity. In a primary implementation, the antigen binding composition comprises an antibody or portion thereof.

The antigen binding compositions of the invention will comprise a scaffold, which supports, orients, and presents antigen-binding complementary determining regions (CDRs) for selective binding with target antigens. The scaffold will comprise a light chain sequence and a heavy chain sequence.

In a primary implementation, the scaffold will comprise a "trastuzumab scaffold," comprising sequences of or derived from the trastuzumab heavy and light chain sequences. "Trastuzumab," as used herein and as known in the art, is an antibody directed to human epidermal growth factor receptor 2 (HER2), for example, as described in Carter et al., Humanization of an anti p185-HER2 antibody for human cancer therapy *Proc. Natl. Acad. Sci.* USA 1992, 89, 4285, and also described in U.S. Pat. No. 6,870,034, Protein Purification, by Breece. The trastazumab light chain reference sequence, from which various antigen binding compositions of the invention are derived, is set forth in SEQ ID NO: 1. The trastazumab heavy chain reference sequence, from which various antigen binding compositions of the invention are derived, set forth in SEQ ID NO: 5. As used herein, a "trastuzumab scaffold" refers to trastuzumab heavy and light chain sequences, excluding any specific complentarity determining regions (CDRs). The trastuzumab scaffold may comprise a light chain sequence of SEQ ID NO: 9, or a subsequence or derivative thereof, and a heavy chain sequence of SEQ ID NO: 10, or a subsequence or derivative thereof.

It will be understood that reference to an enumerated sequence will encompass variants of such sequence. "Variants," as used herein, includes variants of the enumerated sequences, such as variants comprising amino acid substitutions, amino acid additions or deletions, truncations, subsequences and other variations of the enumerated sequence. In various embodiments, variants have at least 75%, at least 80%, at least 90%, at least 95%, or at least 99% sequence identity to the enumerated sequence.

The sequence or subsequence of the antibody scaffold utilized will be determined by the format of the antigen binding composition. In one embodiment, the antigen binding composition of the invention comprises a whole, or substantially whole, antibody. As known in the art, a whole antibody comprises a dimer, each dimer comprising a heavy chain and a light chain. The heavy chain comprises three constant regions, $C_{H2}$ and $C_{H3}$, below the hinge, and $C_{H1}$ above the hinge. The heavy chain also comprises a variable region VH which comprises framework sequences that present the three heavy chain CDRs. The light chain comprises one constant region $C_L$, which is paired with $C_{H1}$, and a variable region $V_L$, comprising framework sequences which contain and present the three light chain CDRs.

In alternative implementations, the antigen binding composition of the invention comprises an antibody fragment, for example, a Fab (Fragment, antigen binding), for example, an antibody fragment which retains target antigen binding ability. In such implementations, the antigen binding composition will comprise a subset of the parts of a whole antibody scaffold, depending on the particular fragment configuration of the composition. In one embodiment, the antibody fragment is an Ig monomer. In one embodiment, the antibody fragment is a Fab (product of papain cleavage) or a Fab' (product of pepsin cleavage), comprising $C_H1$, VH, $V_L$, and $C_L$ sequences and lacking the FC portion of the antibody. In one embodiment, the scaffold comprises the $V_L$ region, for example, nucleotides 1-70, 1-75, 1-80, 1-85, or 1-90 of SEQ ID NO: 9. In one embodiment, the scaffold comprises the VH region, for example, for example, nucleotides 1-70, 1-75, 1-80, 1-85, or 1-90 of SEQ ID NO: 10. In one embodiment, the composition is a F(ab')2 fragment, comprising a Fab' dimer. In one embodiment, the antigen binding composition of the invention comprises a single chain variable fragment (scFv), comprising a fusion protein of the VH and VL sequences of an antibody, wherein the chain sequences are joined by a linker sequence, for example, a linker of 10-50 amino acids, for example about 20-25 amino acids, for example, comprising glycine, serine, and/or threonine.

It will be understood that the scope of the invention encompasses non-trastuzumab scaffold sequences and methionine conjugation sites therein as well. The insights disclosed herein provide the art with tools for the introduction of methionine-mediated functionalization of non-trastuzumab antibodies and antibody fragments at positions equivalent to those disclosed herein for trastuzumab.

CDRs and Target Antigens. The antigen-binding compositions of the invention will comprise CDR sequences which impart binding specificity and affinity for a selected target antigen. The CDRs of the antigen binding compositions of the invention may include all of, or a subset of a CDR-L1 sequence, a CDR-L2 sequence, a CDR-L3 sequence, a CDR-H1 sequence, a CDR-H2 sequence, and a CDR-H3.

In one embodiment, the target antigen is HER2. In such implementations, the CDRs may comprise trastuzumab reference sequence CDRs, e.g. SEQ ID NO: 2 (CDR-L1), SEQ ID NO: 3(CDR-L2), SEQ ID NO: 4 (CDR-L3), SEQ ID NO: 6 (CDR-H1), SEQ ID NO: 7 (CDR-H2) and SEQ ID NO: 8 (CDR-H3). In such implementations, the antigen binding compositions of the invention will comprise improved HER2 targeting compositions utilizing methionine linked functional agents at sites disclosed herein.

In other implementations, the antigen binding compositions of the invention will have affinity and specificity for a non-HER2 target antigen. The target antigen may comprise any species, for example, a protein, a carbohydrate, a nucleic acid, a chemical entity, or any other composition which is targetable by an antibody. Exemplary target antigens include extracellular domains, receptors, and ligands, for example, a target antigen expressed or overexpressed on a cancer cell. Exemplary target antigens include growth factors, receptors thereof, transcription factors, structural proteins and other biological entities implicated in physiological processes and disease.

Specificity and affinity for a selected target antigen may be imparted to the antigen binding compositions of the invention by CDR grafting, or affinity transfer, as known in the art. In some implementations, the antigen binding composition of the invention comprises a trastuzumab scaffold wherein CDRs imparting binding affinity for a selected target antigen have been grafted to the trastuzumab scaffold. Such affinity transfer is readily accomplished by the skilled artisan, for example, by the engineering of nucleic acid sequences coding for light or heavy chain polypeptides of the antigen-binding composition.

Functional moiety. As used herein, a "functional moiety" is a composition of matter that is conjugated to an antigen binding composition by a methionine residue. The functional moiety may comprise any number of compositions. In some implementations, the functional moiety comprises a detection agent, i.e. a species that enables visualization or quantification of the target antigen in a sample or tissue. Detection agents include fluorescent labels, such as a fluorescent protein, fluorescent dye, or fluorophore. Exemplary fluorescent labels include green fluorescent protein, red fluorescent protein, yellow fluorescent protein, fluorescein isothiocyanate, fluorescin, FITC, PE, PerCP, Rhodamine, aminomethylcoumarin, R-phycoerythrin, and fluorochrome dyes, as known in the art. Exemplary fluorescent dyes include ALEXA FLUOR™ (Invitrogen) dyes. In other implementations, the functional moiety may comprise an enzyme for detection and quantification assays, exemplary enzymes including for example, horseradish peroxidase, alkaline phosphatase, urease, and other enzymatic detection systems known in the art.

In some implementations, the functional moiety comprises an affinity tag, an epitope tag for binding of secondary labeled antibodies or other moieties such as agents used in immunofluorescent methods, immunostaining, flow cytometry, and other methods. Other functional moieties include oligonucleotides, such as DNA barcodes.

Antibody Drug Conjugates. In various embodiments, the antigen binding composition of the invention will comprise a antibody drug conjugate, wherein the functional moiety is a therapeutic agent. As used herein, an "antibody drug conjugate" or "ADC" means an antigen binding composition conjugated to one or more drugs or other biologically active agents. In a primary embodiment, the functional moiety of the ADC comprises a cytotoxic agent, for example, for use in the selective inhibition or killing of cancer cells, wherein the ADC selectively targets the cytotoxic agent to cancerous cells, wherein uptake of the cytotoxic agent inhibits the growth of or kills the cell. Any cytotoxic or cytostatic agent may be utilized. Exemplary cytotoxic agents include any cytotoxic or cytostatic composition, including, for example: auristatins, for example, monomethyl auristatin E (MMAE), Monomethyl auristatin F (MMAF), a tubulin inhibitor, a *vinca* alkaloid, a taxane, a DNA-targeting composition, a topoisomerase inhibitor, ENA polymerase II inhibitors, a DNA minor groove binding agent, a DNA minor groove alkylating agent, a nitrogen mustard, an ethyleneimine compound, a growth factor receptor antagonist, vincristine, vinblastine, vindesine, a lexitropsin, a duocarmycin, a taxane, a puromycin, a dolastatin, a maytansinoid, a *vinca* alkaloid, a baccatin derivative, a cryptophysin, a maytansinoid, a combretastatin, or a dolastatin, doxorubicin, daunorubicin, cisplatin, or a radioisotope.

Methionine Linked Compositions. The proteins of the invention will comprise methionine-linked functional moieties. A "methionine-linked functional moiety" is a functional moiety conjugated to a protein by the use of a methionine residue of the protein as a reactive handle, creating what will be referred to herein as a "methionine linkage." Methionine linkage may be achieved by any number of reagents and/or reactions with a methionine residue of the protein. In a primary embodiment, the methionine linkage is achieved by oxaziridine chemistries, as described herein.

The scope of the invention is not limited to oxaziridine-based chemistry and the conjugation of the functional moiety to the protein at the introduced methionine sites of the invention may be by any reaction wherein methionine acts as a reactive handle to which the functional moiety is directly or indirectly bound, linked, conjugated, or otherwise chemically joined, for example, by reagents that interact with the sulfur group of the targeted methionine. Exemplary methionine linkage chemistries include the use of electrophilic reagents to convert methionine to sulfonium salts, for example, as described in Kramer and Deming, Reversible chemoselective tagging and functionalization of methionine containing peptides, Chem Commun. 2013; 49:5144-5146. Other chemistries for conjugation of agents to methionine residues are described in PCT Patent Application Publication Number WO/2018089951, entitled "Redox-Based Reagents for Methionine Bioconjugation," by Chang et al.

Introduced Methionines. In various embodiments, the functional moiety is methionine linked to the protein of the invention by an introduced methionine. As used herein, an "introduced methionine" is a methionine that has been added to a polypeptide at a site where it was not previously found in the original or reference polypeptide sequence. For example, in one embodiment, the scope of the invention encompasses methionine substitutions, wherein a selected non-methionine residue of the reference sequence is substituted with a methionine residue. In an alternative implementation, the methionine is introduced by insertion, i.e., the addition of a methionine at a site it was not found in the reference sequence, between two extant residues of the reference sequence, without deleting any residues. Introduced methionines may be added to a selected protein at a selected site by molecular biology techniques known in the art. In a primary implementation, introduced methionines are created by modification of an expression sequence, e.g. a DNA sequence, wherein a codon for methionine is introduced (e.g. as a substitution or insertion) to a nucleic acid coding for the polypeptide, for example, an AUG codon.

Modifications to the trastuzumab scaffold. The antibody scaffolds of the invention may comprise any number of modifications that enhance the labeling efficiency, stability, or function of the functionalized antigen binding composition. In various embodiments, accessible methionine residues (e.g. oxiziridine-reacting methionine residues) of the selected scaffold light or heavy chain sequence are removed to avoid off-target functionalizations. A "Methionine scrubbed trastuzumab scaffold," as used herein means a trastuzumab scaffold wherein one or more methionines of the reference sequence have been substituted with other non-methionine residues. Advantageously, in antigen-binding compositions comprising heavy chain Fc sequences, removal of certain methionines found in the trastuzumab heavy chain reference sequence prevents unwanted reactions with oxaziridine or other conjugating agents. In one embodiment, the methionine scrubbed scaffold comprises a heavy chain sequence (e.g. a trastuzumab Fc region) wherein the methionine at heavy chain position 252, the methionine at heavy chain position 428, or both the methionines at heavy chain position 252 and 428 are substituted with a non-methionine amino acid. In various embodiments, the non-methionine amino acid is selected from glycine, leucine, or serine.

In another embodiment, the improved trastuzumab scaffold of the invention comprise an "N297 substitution," meaning a heavy chain constant region (e.g trastuzumab heavy chain) wherein the glutamine at position 297 on the heavy chain reference sequence has been substituted with a non-glutamine amino acid. Such substitutions prevent glycosylation of the Fc and enhance or enable oxaziridine functionalization and preserves neonatal receptor binding (FcRn) ability. In various embodiments, the non-glutamine amino acid is selected from glycine, leucine, or serine.

Methods of Conjugating Functional Moieties to Methionines.

In a first aspect, the scope of the invention encompasses novel methods of functionalizing antigen binding polypeptides and other proteins by oxaziridine chemistry. The use of oxaziridine reagents for the functionalization of methionine residues in proteins is known, as described in Lin et al., Redox-based reagents for chemoselective methionine bioconjugation, Science, Science. 2017, 355(6325): 597-602. In oxaziridine based modification of proteins, chemoselective methionine bioconjugation is achieved through redox reactivity, using oxaziridine-based reagents to for rapid, and robust methionine labeling with near-perfect selectivity for methionine residues. FIG. 1A depicts a two-step process for conjugation of a selected agent to a methionine residue by means of oxaziridine reagents. In this process, the target protein is first reacted with a selected oxaziridine to create an alkyne or N3 reactive intermediate. This product is then reacted under suitable conditions, e.g., click chemistry conditions (e.g. copper catalyzed), as known in the art, with a complementary alkyne or azide bearing functional group, to create a stable covalent bond between the protein and functional group. In the method of the invention, the azide-alkyne linkage is facilitated by an oxaziridine composition selected from Table 1.

TABLE 1

Oxaziridine reagents tested for conjugation to introduced methionines.

| oxaziridine compound number | Structure |
|---|---|
| oxaziridine #1 | 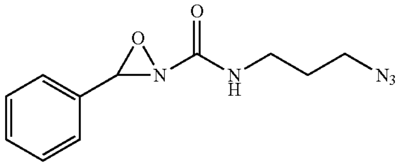 [SMILES: [N-]=[N+]=NCCCNC(=O)N1OC1c1ccccc1] |
| oxaziridine #2 | 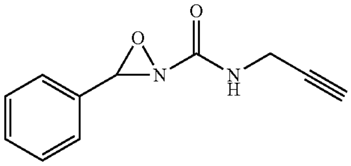 |
| oxaziridine #3 | 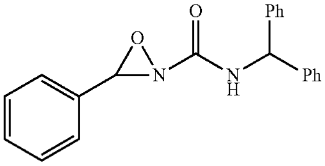 [SMILES: O=C(NC(c1ccccc1)c1ccccc1)N1OC1c1ccccc1] |
| oxaziridine #4 | 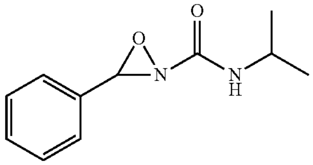 |
| oxaziridine #5 | 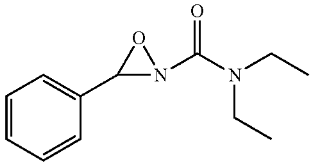 [SMILES: CCN(CC)C(=O)N1OC1c1ccccc1] |
| oxaziridine #6 | 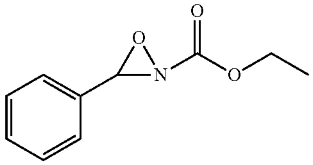 |
| oxaziridine #7 | 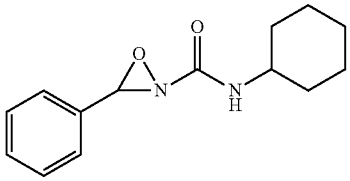 [SMILES: O=C(NC1CCCCC1)N1OC1c1ccccc1] |
| oxaziridine #8 | 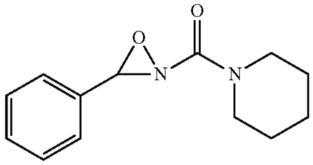 [SMILES: O=C(N1CCCCC1)N1OC1c1ccccc1] |

TABLE 1-continued

Oxaziridine reagents tested for conjugation to introduced methionines.

| oxaziridine compound number | Structure |
|---|---|
| oxaziridine #9 | 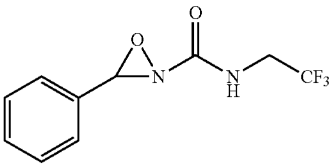 [SMILES: O=C(NCC(F)(F)F)N1OC1c1ccccc1] |
| oxaziridine #10 | 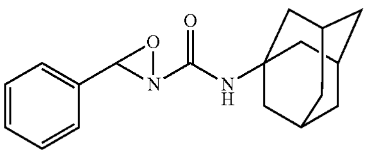 [SMILES: O=C(NC12CC3CC(CC(C3)C1)C2)N1OC1c1ccccc1] |
| oxaziridine #11 | 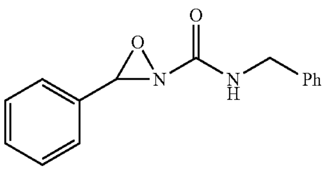 [SMILES: O=C(NCc1ccccc1)N1OC1c1ccccc1] |
| oxaziridine #12 | 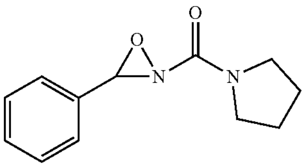 [SMILES: O=C(N1CCCC1)N1OC1c1ccccc1] |
| oxaziridine #13 | 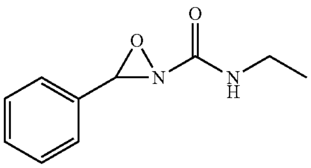 |
| oxaziridine #14 | 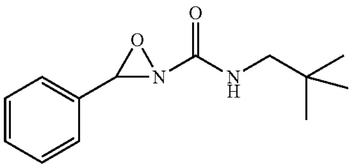 [SMILES: CC(C)(C)CNC(=O)N1OC1c1ccccc1] |
| oxaziridine #15 | 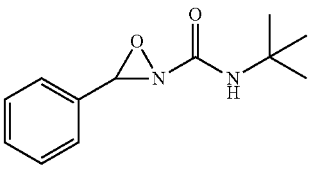 [SMILES: CC(C)(C)NC(=O)N1OC1c1ccccc1] |
| oxaziridine #16 | 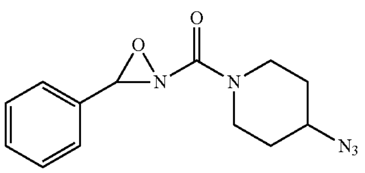 [SMILES: [N-]=[N+]=NC1CCN(C(=O)N2OC2c2ccccc2)CC1] |

In one embodiment the scope of the invention encompasses the composition of matter azide-piperidine oxaziridine,

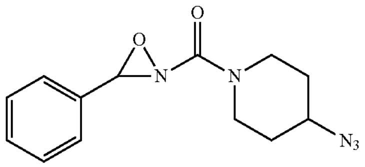 [SMILES: [N-]=[N+]=NC1CCN(C(=O)N2OC2c2ccccc2)CC1]

(Oxaziridine composition #16), for example, azide-piperidine oxaziridine

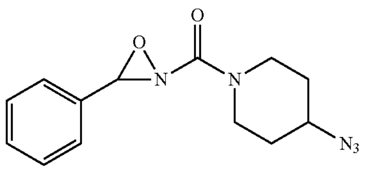 [SMILES: [N-]=[N+]=NC1CCN(C(=O)N2OC2c2ccccc2)CC1]

for use in a method of functionalizing of polypeptides at methionine residues. The synthesis of oxaziridine composition #16 may be achieved by methods as follows. Tert-butyl 4-azidopiperidine-1-carboxylate was synthesized using a previous published procedure described in Weisner et al. Covalent-Allosteric Kinase Inhibitors. *Angew. Chem. Int. Ed. Engl.* 54, 10313-6 (2015). Tert-butyl 4-azidopiperidine-1-carboxylate (10 mmol) was dissolved in MeOH (20 mL) and 4M HCl in 1,4-dioxane (22 mmol, 2.2 equiv.) was added dropwise and the solution was stirred overnight at room temperature. The solution was concentrated in vacuo and a colorless solid formed after washed with diethyl ether (quantitative yield). The crude material was taken on without further purification. 4-azidopiperidinium chloride (10 mmol) was dissolved in water (10 mL) and KOCN (30 mmol, 3 equiv.) was added in one portion. The reaction was stirred at 60° C. for 12 hours and a colorless precipitant formed. The precipitant (4-azidopiperidine-1-carboxamide) was filter, washed with diethyl ether, and was used in the next reaction without any further purification (quantitative yield). THE (30 mL) was added to 4-azidopiperidine-1-carboxamide (1.7 g, 10 mmol, 1 equiv.) and benzaldehyde (1.2 mL, 12 mmol, 1.2 equiv.) was subsequently added. $Ti(OiPr)_4$ (4.1 mL, 14 mmol, 1.4 equiv.) was added and the reaction stirred at room temperature for 4 hours. The solution was concentrated under reduced pressure and was used immediately. mCPBA (75%, 6.9 g, 30 mmol, 3 equiv.) was added to a 1:1 mixture of DCM:sat. $K_2CO_3$ (0.125 M) and was stirred for 10 minutes. Condensation residue (1 equiv.) was dissolved in DCM (1 M) and was added slowly to the mCPBA mixture. The mixture was vigorously stirred for 1 hour and was diluted with $H_2O$ (3× the volume). The biphasic solution was extracted with DCM (3×) and the organic layers combined, washed with brine (1×), dried over $Na_2SO_4$, and was concentrated under reduced pressure. The concentrate was purified using column chromatography (1% $Et_2O$ in DCM) to afford the oxaziridine as a colorless oil (891 mg, 33% yield).

In one embodiment, the method of the invention comprises the steps of reacting a protein containing one or more methionine residues to an oxaziridine composition bearing an azide or other click chemistry group, the oxaziridine composition being selected from oxaziridine #1 to oxaziridine #16. This reaction forms an intermediate azide-bearing species conjugated to the polypeptide by a sulfimide bond formed with the sulfur of the methionine residue(s). Exemplary conditions for the formation of the intermediate are, for example, reaction at room temperature in buffer such as PBS for times of 10-120 minutes, for example, 30-60 minutes. In a second reaction, the intermediate compound is further reacted with a functional molecule bearing an alkyne group under suitable click chemistry conditions (for example, in buffer such as PBS buffer, at room temperature, for 1-10 hours) to form a covalent conjugation between the polypeptide and the functional molecule by an sulfimide linkage. In one embodiment, the oxaziridine composition is oxaziridine #16. In one embodiment, the oxaziridine composition is oxaziridine #8. In one embodiment, the oxaziridine composition is oxaziridine #5.

In various embodiments, the ratio of oxaziridine reagent to protein substrate is between 1:1 to 50:1. A ratio of 5:1 oxaziridine reagent may be effective for efficient functionalization (e.g. yields of greater than 80%) in the case of highly accessible methionines. In the case of less accessible, partially buried methionines, higher ratios of reagent to protein may be necessary, for example, 10:1, 15:1, 20:1 or 25:1.

Methionine Sites for Functionalization. The inventors of the present disclosure have advantageously identified various sites on Ig scaffolds (e.g. the trastuzumab scaffold) that can be substituted with methionine residues for the conjugation of functional moieties. Funcationalizions at these targeted sites have various desirable qualities. First, functionalization at the sites disclosed herein may be achieved with high efficiency, for example, at least 60%, at least 70%, at least 80%, at least 90% or at least 95% labeling efficiency. Additionally, functionalization at the sites disclosed herein creates highly stable conjugates (e.g. resistant to hydrolysis), wherein retention of functional moiety and/or functional moiety activity are retained at least 60%, at least 70%, at least 80%, or at least 90% for several days following functionalization (e.g., three days, five days, ten days, twenty days, fifty days, or one hundred days). In some embodiments, functional moieties and/or their activity are retained at physiological temperatures (e.g. 37° C.) and are resistant to hydrolysis under in vivo conditions. Furthermore, functionalization at the scaffold light and heavy chain positions disclosed herein does not interfere with antigen binding activity, maintaining or enhancing affinity for the target species, for example, retaining at last 60%, at least 70%, at least 80%, or at least 90% affinity for the target antigen of the composition.

In one aspect, the scope of the invention encompasses an antigen binding composition comprising an introduced methionine substitution at one or more sites listed in Table 2, Table 3, and/or Table 4.

TABLE 2

Table 2 lists the solvent accessibility, labeling efficiency, yield, conjugation stability, affinity, and thermostability of oxaziridine-methionine conjugates for trastuzumab scaffold methionine substitutions at solvent accessible sites. Methionine substitution positions are listed with respect to trastuzumab sequence, Kabat position, and position in SEQ ID NO: 9 (light chain) and SEQ ID NO: 10 (heavy chain).

| Position | Res | Kabat | SEQ ID 9 | SEQ ID 10 | ASA | Yield mg | % Label | $K_d$ Pre | $K_d$ Post | Therm Stab Pre | Therm Stab Post |
|---|---|---|---|---|---|---|---|---|---|---|---|
| rAB1001 | — | — | | | 0.00 | 8.0 | 0 | 88 | 197 | 82.5 | 82.6 |
| LC-Cmet | — | — | | | 0.67 | 7.2 | 93 | 129 | 183 | 82.4 | 82.2 |
| LC001 | D | 1 | 1 | | 0.94 | 7.1 | 76 | 118 | 293 | 83.2 | 82.5 |
| LC003 | Q | 3 | 3 | | 0.95 | 0.0 | 85 | 138 | 58 | 82.5 | 82.2 |
| LC007 | S | 7 | 7 | | 0.98 | 5.4 | 96 | 111 | 150 | 82.6 | 81.5 |
| LC009 | S | 9 | 9 | | 0.86 | 16.9 | 93 | 96 | 339 | 81.9 | 81.5 |
| LC010 | S | 10 | 10 | | 0.73 | 7.2 | 94 | 50 | 189 | 82.9 | 82.2 |
| LC012 | S | 12 | 12 | | 0.67 | 8.3 | 63 | 115 | 169 | 81.7 | 80.3 |
| LC014 | S | 14 | 14 | | 0.90 | 6.4 | 93 | 112 | 162 | 82.3 | 81.8 |
| LC018 | R | 18 | 18 | | 0.86 | 10.9 | 80 | 80 | 246 | 82.0 | 81.2 |
| LC020 | T | 20 | 20 | | 0.71 | 9.6 | 95 | 80 | 183 | 81.8 | 80.6 |
| LC041 | G | 41 | 30 | | 0.92 | 7.3 | 95 | 132 | 175 | 81.7 | 82.4 |
| LC042 | K | 42 | 31 | | 0.79 | 7.8 | 87 | 101 | 155 | 81.8 | 81.2 |
| LC045 | K | 45 | 34 | | 0.73 | 5.9 | 93 | 167 | 216 | 80.9 | 79.9 |
| LC057 | G | 57 | 39 | | 0.94 | 9.1 | 93 | 123 | 252 | 80.3 | 79.9 |
| LC060 | S | 60 | 42 | | 1.00 | 6.3 | 92 | 125 | 267 | 81.7 | 81.0 |
| LC065 | S | 65 | 47 | | 0.90 | 11.8 | 92 | 82 | 285 | 81.6 | 81.5 |
| LC067 | S | 67 | 49 | | 1.00 | 6.6 | 94 | 120 | 205 | 82.2 | 81.9 |
| LC068 | G | 68 | 50 | | 0.90 | 6.5 | 91 | 88 | 191 | 80.2 | 79.6 |
| LC069 | T | 69 | 51 | | 0.83 | 11.4 | 69 | 103 | 170 | 82.3 | 81.7 |
| LC076 | S | 76 | 58 | | 0.74 | 6.3 | 82 | 135 | 175 | 81.9 | 80.7 |
| LC081 | E | 81 | 63 | | 0.69 | 6.4 | 84 | 116 | 213 | 79.9 | 78.8 |
| LC085 | T | 85 | 67 | | 0.68 | 8.3 | 61 | 118 | 147 | 81.6 | 80.2 |
| LC100 | Q | 100 | 73 | | 0.86 | 5.2 | 90 | 116 | 74 | 81.1 | 80.9 |
| LC107 | K | 107 | 80 | | 0.84 | 5.1 | 90 | 148 | 149 | 81.5 | 80.1 |
| LC108 | R | 108 | 81 | | 0.80 | 0.0 | — | — | — | — | — |
| LC112 | A | 112 | 85 | | 0.73 | 6.4 | 88 | 94 | 201 | 80.2 | 77.7 |
| LC114 | S | 114 | 87 | | 0.83 | 4.7 | 89 | 165 | 207 | 82.5 | 81.3 |
| LC123 | E | 123 | 96 | | 0.76 | 8.1 | 57 | 147 | 183 | 82.3 | 81.8 |
| LC126 | K | 126 | 99 | | 0.87 | 7.7 | 87 | 97 | 198 | 82.3 | 82.3 |
| LC128 | G | 128 | 101 | | 0.98 | 6.5 | 90 | 94 | 177 | 81.6 | 81.3 |
| LC143 | E | 143 | 116 | | 0.94 | 7.6 | 87 | 129 | 138 | 81.8 | 81.5 |
| LC145 | K | 145 | 118 | | 0.82 | 6.3 | 93 | 93 | 190 | 82.4 | 82.2 |
| LC152 | N | 152 | 125 | | 0.71 | 4.3 | 88 | 95 | 192 | 82.0 | 82.1 |
| LC156 | S | 156 | 129 | | 0.99 | 9.8 | 89 | 124 | 190 | 82.6 | 82.3 |
| LC157 | G | 157 | 130 | | 1.00 | 7.4 | 86 | 116 | 223 | 82.0 | 82.0 |
| LC160 | Q | 160 | 133 | | 0.77 | 4.8 | 58 | 94 | 169 | 82.7 | 80.6 |
| LC168 | S | 168 | 141 | | 0.92 | 0.0 | | | | | |

TABLE 2-continued

Table 2 lists the solvent accessibility, labeling efficiency, yield, conjugation stability, affinity, and thermostability of oxaziridine-methionine conjugates for trastuzumab scaffold methionine substitutions at solvent accessible sites. Methionine substitution positions are listed with respect to trastuzumab sequence, Kabat position, and position in SEQ ID NO: 9 (light chain) and SEQ ID NO: 10 (heavy chain).

| Position | Res | Kabat | SEQ ID 9 | SEQ ID 10 | ASA | Yield mg | % Label | $K_d$ Pre | $K_d$ Post | Therm Stab Pre | Therm Stab Post |
|---|---|---|---|---|---|---|---|---|---|---|---|
| LC169 | K | 169 | 142 | | 1.00 | 5.1 | 92 | 264 | 179 | 82.0 | 81.9 |
| LC182 | S | 182 | 155 | | 0.90 | 8.1 | 89 | 92 | 168 | 82.3 | 81.6 |
| LC184 | A | 184 | 157 | | 0.94 | 3.6 | 71 | 110 | 148 | 82.3 | 82.2 |
| LC190 | K | 190 | 163 | | 1.00 | 4.4 | 94 | 227 | 202 | 82.5 | 82.3 |
| LC202 | S | 202 | 175 | | 0.92 | 6.8 | 93 | 103 | 237 | 82.3 | 82.2 |
| LC203 | S | 203 | 176 | | 1.00 | 6.3 | 92 | 211 | 152 | 82.3 | 82.2 |
| LC205 | V | 205 | 178 | | 0.76 | 7.7 | 71 | 97 | 190 | 82.1 | 80.8 |
| LC210 | N | 210 | 183 | | 0.72 | 7.6 | 88 | 79 | 178 | 82.6 | 82.4 |
| HC001 | E | 1 | | 1 | 0.78 | 6.3 | 92 | 101 | 141 | 82.3 | 82.2 |
| HC003 | Q | 4 | | 3 | 0.85 | 4.5 | 94 | 94 | 149 | 82.5 | 82.6 |
| HC005 | V | 5 | | 5 | 0.89 | 4.9 | 96 | 139 | 111 | 82.4 | 82.5 |
| HC007 | S | 7 | | 7 | 0.95 | 7.4 | 95 | 128 | 156 | 82.3 | 82.6 |
| HC008 | G | 8 | | 8 | 0.72 | 5.2 | 95 | 141 | 189 | 81.2 | 81.0 |
| HC010 | G | 10 | | 10 | 0.97 | 7.2 | 85 | 113 | 219 | 81.5 | 81.1 |
| HC013 | Q | 13 | | 13 | 0.69 | 4.1 | 89 | 133 | 138 | 82.1 | 81.7 |
| HC015 | G | 15 | | 15 | 0.98 | 4.9 | 92 | 114 | 170 | 81.8 | 81.6 |
| HC017 | S | 17 | | 17 | 0.75 | 5.2 | 96 | 84 | 137 | 81.9 | 82.0 |
| HC019 | R | 19 | | 19 | 0.86 | 4.3 | 88 | 83 | 47 | 82.3 | 81.9 |
| HC023 | A | 23 | | 23 | 0.86 | 5.2 | 94 | 54 | 153 | 82.6 | 82.6 |
| HC042 | G | 42 | | 32 | 1.00 | 5.4 | 96 | 143 | 183 | 81.8 | 82.2 |
| HC043 | K | 43 | | 33 | 0.89 | 6.3 | 87 | 122 | 122 | 82.3 | 81.5 |
| HC044 | G | 44 | | 34 | 0.72 | 7.9 | 94 | 72 | 165 | 80.0 | 78.7 |
| HC046 | E | 46 | | 46 | 0.89 | 6.3 | 85 | 93 | 169 | 82.0 | 81.3 |
| HC066 | G | 65 | | | 1.00 | 5.8 | 92 | 216 | 155 | 82.0 | 81.8 |
| HC069 | T | 68 | | 42 | 0.84 | 7.3 | 94 | 95 | 187 | 82.2 | 82.3 |
| HC071 | S | 70 | | 44 | 0.84 | 6.0 | 82 | 130 | 197 | 82.2 | 81.8 |
| HC075 | S | 74 | | 48 | 0.90 | 7.0 | 93 | 126 | 177 | 82.2 | 82.2 |
| HC076 | K | 75 | | 49 | 0.88 | 10.2 | 93 | 129 | 224 | 82.0 | 82.2 |
| HC077 | N | 76 | | 50 | 0.74 | 5.4 | 94 | 64 | 139 | 81.2 | 80.9 |
| HC084 | N | 82A | | 58 | 0.79 | 6.7 | 95 | 110 | 151 | 81.9 | 82.0 |
| HC085 | S | 82B | | 59 | 0.77 | 6.9 | 94 | 86 | 134 | 82.3 | 82.3 |
| HC087 | R | 83 | | 61 | 0.71 | 7.0 | 93 | 96 | 193 | 82.2 | 82.0 |
| HC112 | Q | 105 | | 75 | 0.85 | 8.8 | 96 | 76 | 168 | 82.0 | 82.1 |
| HC119 | S | 112 | | 82 | 0.72 | 4.9 | 93 | 91 | 136 | 79.5 | 79.2 |
| HC120 | S | 113 | | 83 | 0.70 | 6.0 | 78 | 105 | 137 | 82.4 | 82.3 |
| HC122 | S | 115 | | 85 | 1.00 | 6.2 | 92 | 90 | 155 | 82.0 | 82.1 |
| HC124 | K | 117 | | 87 | 0.82 | 4.4 | 92 | 108 | 217 | 81.8 | 81.6 |
| HC127 | S | 120 | | 90 | 0.74 | 7.2 | 88 | 78 | 214 | 82.3 | 81.9 |
| HC137 | S | 130 | | 100 | 0.97 | 7.2 | 88 | 72 | 188 | 82.2 | 81.2 |
| HC139 | S | 134 | | 102 | 1.00 | 7.2 | 93 | 84 | 163 | 82.3 | 82.0 |
| HC141 | G | 136 | | 104 | 0.92 | 5.0 | 94 | 114 | 177 | 82.3 | 82.3 |
| HC142 | T | 137 | | 105 | 0.92 | 8.0 | 95 | 91 | 148 | 82.4 | 81.4 |
| HC151 | D | 146 | | 114 | 0.76 | 3.0 | 49 | 94 | 138 | 68.8 | 69.9 |
| HC158 | T | 153 | | 121 | 0.71 | 5.5 | 95 | 97 | 136 | 82.2 | 81.7 |
| HC163 | S | 163 | | 126 | 0.99 | 17.7 | 94 | 74 | 177 | 82.0 | 82.4 |
| HC164 | G | 164 | | 127 | 0.99 | 4.4 | 94 | 106 | 144 | 80.9 | 80.3 |
| HC168 | S | 168 | | 131 | 1.00 | 4.6 | 93 | 125 | 94 | 82.2 | 82.2 |
| HC179 | S | 180 | | 142 | 0.98 | 2.8 | 91 | 117 | 125 | 82.0 | 81.8 |
| HC180 | S | 182 | | 143 | 0.73 | 2.8 | 92 | 161 | 158 | 80.9 | 80.3 |
| HC181 | G | 183 | | 144 | 0.97 | 3.7 | 97 | 126 | 160 | 81.5 | 82.4 |
| HC194 | S | 196 | | 157 | 0.98 | 4.6 | 90 | 107 | 90 | 82.2 | 82.0 |
| HC197 | G | 199 | | 160 | 0.77 | 4.2 | 92 | 166 | 191 | 82.5 | 82.4 |
| HC198 | T | 200 | | 161 | 0.94 | 4.0 | 94 | 122 | 134 | 82.2 | 81.9 |
| HC202 | I | 207 | | 165 | 0.73 | 5.0 | 35 | 72 | 157 | 81.9 | 81.2 |
| HC206 | N | 211 | | 169 | 0.92 | 5.7 | 94 | 110 | 144 | 82.5 | 81.8 |
| HC211 | N | 216 | | 174 | 1.00 | 10.1 | 85 | 74 | 192 | 82.2 | 82.3 |
| HC213 | K | 218 | | 176 | 0.99 | 6.7 | 91 | 89 | 126 | 82.3 | 82.1 |
| HC222 | S | 229 | | 185 | 0.88 | 7.8 | 91 | 113 | 128 | 82.5 | 82.5 |

TABLE 3

Table 3 lists the solvent accessibility, yield, affinity, conjugation stability at 5X and 20X oxaziridine, and thermostability of oxaziridine-methionine conjugates for trastuzumab scaffold methionine substitutions at less solvent accessible sites. Methionine substitution positions are listed with respect to trastuzumab sequence, Kabat position, and position in SEQ ID NO: 9 (light chain) and SEQ ID NO: 10 (heavy chain).

| Site | Residue | Kabat | SEQ ID NO 9 | SEQ ID NO 10 | ASA | Yield mg/L | $K_d$ pM | Thermo-stability ° C. | % Labeling 5x | % Labeling 20x | % -Stability 37° C. |
|---|---|---|---|---|---|---|---|---|---|---|---|
| LC022 | T | 22 | 22 | | 0.36 | 11.9 | 770 | 82.3 | 92 | — | 42 |
| LC063 | S | 63 | 45 | | 0.52 | 10.8 | 190 | 81.9 | 76 | — | 59 |
| LC066 | R | 66 | 48 | | 0.40 | 6.9 | 780 | 82.7 | 68 | 91 | 99 |
| LC069 | T | 69 | 51 | | 0.83 | 21.8 | 450 | 82.7 | 55 | 84 | 62 |
| LC070 | D | 70 | 52 | | 0.40 | 0.4 | 230 | 82.8 | — | — | — |
| LC072 | T | 72 | 54 | | 0.56 | 0.5 | 270 | 82.2 | — | — | — |
| LC074 | T | 74 | 56 | | 0.44 | 31.2 | 820 | 81.4 | 47 | 83 | 96 |
| LC147 | Q | 147 | 120 | | 0.48 | 25.5 | 490 | 82.5 | 61 | 85 | 49 |
| LC148 | W | 148 | 121 | | 0.10 | 2.0 | 630 | 75.6 | 0 | — | — |
| LC149 | K | 149 | 122 | | 0.27 | 3.2 | 520 | 82.3 | 55 | — | 88 |
| LC192 | Y | 192 | 165 | | 0.12 | 0.5 | 290 | 78.2 | — | — | — |
| LC193 | A | 193 | 166 | | 0.46 | 13.3 | 430 | 81.8 | 0 | — | — |
| LC195 | E | 195 | 168 | | 0.49 | 49.7 | 430 | 82.4 | 70 | 87 | 55 |
| LC208 | S | 208 | 181 | | 0.57 | 5.9 | 380 | 82.4 | 0 | — | — |
| HC018 | L | 18 | 18 | | 0.46 | 33.2 | 650 | 82.6 | 0 | — | — |
| HC021 | S | 21 | | 18 | 0.54 | 36.7 | 530 | 82.3 | 52 | 78 | 87 |
| HC025 | S | 25 | | 25 | 0.42 | 17.2 | 800 | 82.7 | 81 | — | 65 |
| HC082 | Q | 81 | | 56 | 0.67 | 0.0 | — | — | — | — | — |
| HC201 | Y | 206 | | 164 | 0.13 | 22.4 | 720 | 81.0 | 0 | — | — |
| HC204 | N | 209 | | 167 | 0.47 | 5.1 | 730 | 81.7 | 84 | — | 46 |
| HC212 | T | 217 | | 175 | 0.26 | 23.7 | 18200 | 81.8 | 62 | 83 | 95 |
| HC215 | D | 220 | | 178 | 0.49 | 21.3 | 550 | 80.8 | 85 | — | 55 |
| HC217 | K | 222 | | 180 | 0.64 | 20.5 | 530 | 82.3 | 62 | 84 | 60 |

TABLE 4

Table 4 lists the labeling efficiency and thermostability of oxaziridine-methionine conjugates for trastuzumab scaffold methionine Fc substitutions. Methionine substitution positions are listed with respect to trastuzumab sequence, Kabat position, and position in SEQ ID NO: 10 (heavy chain).

| Site | Residue | Kabat | SEQ ID NO 10 | Aligned Fab site | % labeling | % stability |
|---|---|---|---|---|---|---|
| HC262 | V | 275 | 225 | HC.S21 | 86 | 100 |
| HC292 | R | 309 | 255 | LC.R66 | 80 | 74 |
| HC307 | T | 326 | 270 | LC.T74 | 0 | — |
| HC382 | E | 407 | 345 | LC.K149 | 61 | 90 |
| HC437 | T | 468 | 400 | HC.T212 | 0 | — |

In a primary embodiment, a single introduced methionine is present in the antigen binding composition. In various alternative embodiments, two or more introduced methionines are present in the antigen binding composition, for example, two, three, four, five, six, seven, eight, nine, ten or more introduced methionines selected from Table 2, Table 3, and/or Table 4.

In a primary aspect, the methionine substitutions of the invention are implemented in a trastuzumab scaffold, for example, a trastuzumab light chain comprising SEQ ID NO: 9 or a variant thereof, and/or a trastuzumab heavy chain comprising SEQ ID NO: 10 or a variant thereof.

In an alternative aspect, the scope of the invention encompasses the introduction of methionines, and subsequent conjugates formed therewith, at equivalent positions in non-trastuzumab sequences. While the sites identified in Tables 2, 3 and 4 were developed using trastuzumab scaffolds, the skilled artisan will recognize that the novel substitution sites disclosed herein may be applied in similar light and heavy chain sequences. The trastuzumab light and heavy chain scaffold sequences were developed based on human Ig sequences. The methionine substitution sites identified herein may be applied in the modification of antibody scaffolds having high sequence similarity to trastuzumab light and heavy chain sequences, including human Ig sequences, human Ig subclass 1 sequences, human Ig (1) kappa sequences, humanized Ig sequences, and scaffold sequences of heavy and light chains from antibodies including rituximab, alemtuzumab, cetuximab, bevacizumab, panitumumab, ofatumumab, ipilimumab, pertuzumab, obinutuzumab, ramucirumab, pembrolizumab, nivolumab, dinutuximab, daratumumab, necitumumab, elotuzumab, atezolizumab, olaratumab, avelumab, and durvalumab. Positions equivalent to the novel methionine functionalization sites disclosed herein may be derived by any number of alignment tools known in the art, for example, IGBLAST, ABYSIS, PYMOL or like analysis tools.

In certain embodiments, the scope of the invention encompasses novel ADCs based on the modification of existing therapeutic antibodies, for example, comprising an antibody selected from rituximab, alemtuzumab, cetuximab, bevacizumab, panitumumab, ofatumumab, ipilimumab, pertuzumab, obinutuzumab, ramucirumab, pembrolizumab, nivolumab, dinutuximab, daratumumab, necitumumab, elotuzumab, atezolizumab, olaratumab, avelumab, and durvalumab or an antigen binding fragment thereof, wherein one more methionine substitutions is made at a position selected from Table 2, Table 3, or Table 4, or an equivalent position, and wherein a functional moiety is conjugated at the selected position, for example, a therapeutic moiety, for example, a cytotoxic agent.

In various embodiments, the scope of the invention encompasses an antigen binding composition comprising a light chain sequence (e.g. a trastuzumab light chain sequence). In one embodiment, the one or more substitutions comprises introduced methionine at a solvent accessible site selected from Table 2. Exemplary substitutions include LC.S7M, LC.T20M, LC.G41M, LCK145M, LC.K190M, and LCS202M. In another embodiment, the one or more substitutions comprises introduced methionine at a partially buried (less solvent accessible) site selected from Table 3, for example, methionine substitutions LC.T22M, LC.S63M, LC.R66M, LC.T74M, LC.Q147M, LC.K149M, and LC.E195M.

In various embodiments, the scope of the invention encompasses an antigen binding composition comprising heavy chain sequence (e.g. a trastuzumab heavy chain sequence). In one embodiment, the one or more substitutions comprises introduced methionine at a solvent accessible site selected from Table 2, for example, methionine substitutions HC.G42M, HC.S85M, HC.Q112M, HC.S163M, HCG181M, and HC.T198M. In another embodiment, the one or more substitutions comprises introduced methionine at a partially buried (less solvent accessible) site selected from Table 3, for example, methionine substitutions HCS21M, HC.S25M, HC.N204M, HC.D215M, and HC.K217M.

In one embodiment, the antigen binding composition of the invention comprises an Fc sequence comprising a heavy chain sequence (e.g. a trastuzumab heavy chain Fc sequence). In various embodiments, the Fc sequence comprises one or more substitutions selected from Table 4, for example, HC.V262M, HC.R292M, or HC.E382M. The heavy chain sequence may comprise additional modifications, including one or more of HC.M252, is substituted with a non-methionine amino acid; HC.M428 substituted with a non-methionine amino acid; and HC.N297 substituted with a non-glutamine amino acid.

In another aspect, the scope of the invention encompasses an antigen binding composition comprising a functional moieties conjugated to the foregoing introduced methionine residues. In various embodiments, the scope of the invention encompasses a functionalized antigen binding composition comprising one or more methionine linked functional moieties, wherein the one or more methionine linked functional moiety is conjugated at a site selected from Table 2, Table 3, or Table 4. Exemplary conjugates include functionalization at methionine substitutions LC.S7M, LC.T20M, LC.G41M, LCK145M, LC.K190M, LCS202M, LC.T22M, LC.S63M, LC.R66M, LC.T74M, LC.Q147M, LC.K149M, LC.E195M, HC.G42M, HC.S85M, HC.Q112M, HC.S163M, HCG181M, HC.T198M, HCS21M, HC.S25M, HC.N204M, HC.D215M, HC.K217M, HC.V262M, HC.R292M, or HC.E382M.

Nucleic Acids, Engineered Cells. In another aspect, the scope of the invention further encompasses nucleic acid constructs which code for the antigen binding compositions of the invention. The nucleic acids may comprise expression vectors, plasmids, and/or genomes of cells engineered to express the polypeptide elements of the invention, e.g. light and heavy chain sequences wherein one or both of the light or heavy chain sequences comprises an introduced methionine, for example, an introduced methionine at a site selected from Table 2, Table 3, or Table 4. The nucleic acid constructs of the invention may be coded utilizing codons optimized for expression in any host, including humans or other organisms such as yeast, insect cells, Cho cells, other rodent cells, bacterial cells and others.

In one implementation, the scope of the invention encompasses cells transformed with a nucleic acid construct of the invention such that the cell will express an antigen binding composition of the invention comprising one or more introduce methionines. In one embodiment, the transformed cells comprise human cells. In one embodiment, the transformed cells comprise rodent (e.g. mouse, rat, rabbit, CHO cells, etc.) cells. In one embodiment, the transformed cells comprise yeast, bacterial, insect, or other cells utilized as expression vectors. In one embodiment, the transformed cells comprise hybridomas.

Methods of Use. The scope of the invention further encompasses methods of using the various compositions of matter disclosed herein. In one implementation, the antigen binding composition of the invention comprises a functional moiety wherein the functional moiety is a therapeutic agent. In one embodiment, the therapeutic agent is a cytotoxic agent. In one implementation, the scope of the invention encompasses a method of treatment, comprising administration of a therapeutically effective amount of an antigen-binding polypeptide which selectively binds a target species associated with a disease state, to a subject in need of treatment (e.g. a human subject) wherein the antigen-binding polypeptide comprises one or more methionine linked therapeutic agents, wherein the one or more methionine linked therapeutic agents is conjugated to the polypeptide at a position selected from Table 2, Table 3, or Table 4. In one embodiment, the therapeutic agent is a cytotoxic agent and the disease state is a proliferative disease, e.g., cancer.

In another implementation, the scope of the invention encompasses detection methods. In one embodiment, the functional moiety of the functionalized antigen binding composition is a detection agent. In this implementation, the scope of the invention encompasses a method of detecting a target species in sample, comprising contacting the sample with an antigen-binding composition which selectively binds the target species and which comprises one or more methionine linked detection agents, wherein the one or more methionine linked detection agents is conjugated at a position selected from Table 1, Table 2, or Table 3. In various embodiments, the sample may comprise a mixture of cells, a tissue, an organism, or a sample such as blood, serum, biopsy material, or an environmental sample. In one embodiment, the detection agent is a reporter, fluorescent moiety, imaging agent, or other composition of matter that signals the presence or abundance of the target species.

Exemplary Embodiments

In certain embodiments, the scope of the invention encompasses an antigen binding composition, comprising an antibody scaffold; wherein the scaffold comprises one or more complementarity determining region sequences that impart binding affinity for a selected target antigen; and wherein the scaffold comprises one or more introduced methionine residues: wherein each of the one or more introduced methionine residues is present at a selected site in the scaffold selected from Table 2, Table 3, or Table 4; and wherein a functional molecule is conjugated to each of the one or more introduced methionine residues, wherein the scaffold comprises wherein the scaffold is a trastuzumab scaffold, in one embodiment, the trastuzumab scaffold comprises: a polypeptide comprising at least 95% sequence identity to SEQ ID NO: 9; and a polypeptide comprising at least 95% sequence identity to SEQ ID NO: 10; wherein the antigen binding composition comprises a whole antibody, an immunoglobulin monomer, or an antigen-binding antibody fragment, a human IgG scaffold or subsequence thereof, a human IgG1 scaffold or subsequence thereof, an Fc sequence, a methionine scrubbed Fc sequence, a methionine scrubbed sequence comprising any of the methionine of SEQ ID NO: 10 position 218 (HC.M252) is substituted with a non-methionine amino acid; the methionine of SEQ ID NO: 10 position 394 (HC.M428) is substituted with a non-methionine amino acid; or an Fc sequence wherein the glutamine of SEQ ID NO: 10 position 363 (N.297) is substituted with a non-glutamine amino acid. In various embodiments, the one or more introduced methionines is introduced at SEQ ID NO: 9 residue 48; the one or more introduced methionines is introduced at SEQ ID NO: 9 residue 56 (LC.T74M); the one or more introduced methionines is introduced at SEQ ID NO: 9 residue 122 (LC.K149M); the one or more introduced methionines is introduced at SEQ ID NO: 10 residue 21 (HC.S21M); the one or more introduced methionines is introduced at SEQ ID NO: 10 residue 225 (HC.V262M); the one or more introduced methionines is introduced at SEQ ID NO: 10 residue 258 (HC.R292M): in various embodiments, the functional molecule conjugated to each of the one or more introduced methionine residues is conjugated to the introduced methionine by oxaziridine-mediated conjugation, in various embodiments the oxaziridine-mediated conjugation is achieved by the use of an oxaziridine selected from the group consisting of

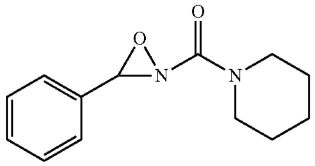
,

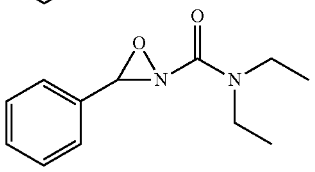
, and

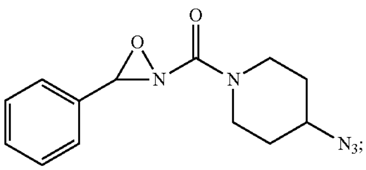 [SMILES: [N-]=[N+]=NC1CCN(C(=O)N2OC2c2ccccc2)CC1]
;

in various embodiments, the functional molecule conjugated to each of the one or more introduced methionine residues comprises a therapeutic agent; in various embodiments, the functional molecule conjugated to each of the one or more introduced methionine residues comprises a therapeutic agent a cytotoxic agent; in various embodiments, the functional molecule conjugated to each of the one or more introduced methionine residues comprises a detection agent; in various embodiments, the functional molecule conjugated to each of the one or more introduced methionine residues comprises an epitope tag; in various embodiments, the one or more CDRs are grafted from another antibody to confer affinity to a selected target antigen.

In other implementations, the scope of the invention encompasses a modified antibody or antigen binding fragment thereof comprising one or more introduced methionine residues present at a selected site in the scaffold of the antibody or antigen binding fragment thereof, wherein the one or more sites is selected from Table 2, Table 3, or Table 4, or an equivalent site thereof; and wherein a functional molecule is conjugated to each of the one or more introduced methionine residues, wherein the antibody comprises trastuzumab, SEQ ID NO: 1, SEQ ID NO: 5, or an antibody selected from rituximab, alemtuzumab, cetuximab, bevacizumab, panitumumab, ofatumumab, ipilimumab, pertuzumab, obinutuzumab, ramucirumab, pembrolizumab, nivolumab, dinutuximab, daratumumab, necitumumab, elotuzumab, atezolizumab, olaratumab, avelumab, and durvalumab; in various embodiments, the functional molecule conjugated to each of the one or more introduced methionine residues is conjugated to the introduced methionine by oxaziridine-mediated conjugation, in various embodiments the oxaziridine-mediated conjugation is achieved by the use of an oxaziridine selected from the group consisting of

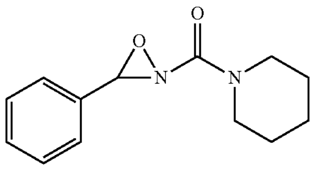
,

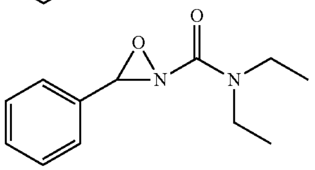
, and

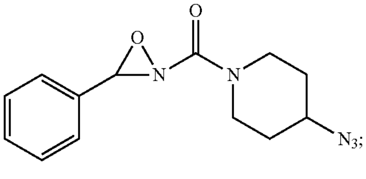 [SMILES: [N-]=[N+]=NC1CCN(C(=O)N2OC2c2ccccc2)CC1]
;

in various embodiments, the functional molecule conjugated to each of the one or more introduced methionine residues comprises a therapeutic agent; in various embodiments, the functional molecule conjugated to each of the one or more introduced methionine residues comprises a therapeutic agent, in one embodiment, the therapeutic agent is a cytotoxic agent; in various embodiments, the functional molecule conjugated to each of the one or more introduced methionine residues comprises a detection agent; in various embodiments, the functional molecule conjugated to each of the one or more introduced methionine residues comprises an epitope tag In various embodiments, the scope of the invention encompasses a method of functionalizing a polypeptide comprising one or more methionine residues with a selected composition, comprising the steps of reacting the polypeptide with an oxaziridine composition comprising an oxaziridine selected from the group consisting of

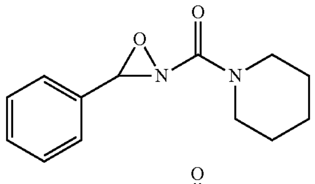

,

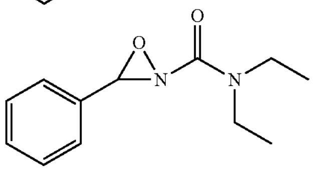

, and

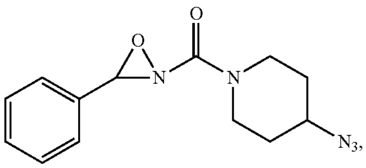 [SMILES: [N-]=[N+]=NC1CCN(C(=O)N2OC2c2ccccc2)CC1]

, under suitable conditions for the formation of a an intermediate composition comprising a sulfimide bond; and performing a second reaction with the selected composition under suitable conditions for azide-alkyne reaction, wherein the selected composition comprises an alkyne group, thereby conjugating the selected composition to the polypeptide by sulfimide linkage; in various embodiments, the polypeptide is integral to an antigen binding composition comprising an antibody or antigen binding fragment thereof; in various embodiments, the selected composition is a therapeutic agent or detection agent.

EXAMPLES

Example 1. Systematic Identification of Engineered Methionines and Oxaziridines for Efficient, Stable, and Site-Specific Antibody Bioconjugation High-throughput scan of the top 95 most accessible sites on the trastuzumab scaffold. Trastuzumab was chosen as the antibody scaffold for the studies for a number of reasons. The trastuzumab framework is popular for humanization due to its high stability, high expression in mammalian cells, high developability, and broad use that is now utilized in parts of three different approved antibody drugs (trastuzumab, bevacizumab, and omalizumab) and the TDM-1 anti-Her2 ADC (ado-trastuzumab emantisine). Synthetic complementarity-determining region (CDR) libraries have been constructed on the trastuzumab scaffold and used by the Recombinant Antibody Network for industrialized recombinant antibody generation to over 500 protein targets. The Fab arms in trastuzumab contain three methionines that are buried. Indeed previous studies from the inventors of the present disclosure showed these buried methionines to be unreactive to ReACT, but when a single Met was attached to the C-terminus of the light chain it was found that it could be labeled quantitatively with a simple oxaziridine reagent and conjugated with a fluorophore. While this site can be labelled quantitatively and could be useful for short-term in vitro studies, it was found by the inventors of the present disclosure to become extensively (>80%) hydrolyzed over three days at 37° C. and thus is not suitable for long-term studies or ADC development.

To expand the use of ReACT for antibody bioconjugations, it was sought to systematically determine how methionine mutation, site of labeling, and compound nature affects expression, labeling efficiency, binding affinity, and stability of the antibody. First, efforts were focused on exposed sites on a well characterized aGFP antibody built on the trastuzumab scaffold as a model for ease of assay, as described in Hornsby et al. A High Through-put Platform for Recombinant Antibodies to Folded Proteins. *Mol. Cell. Proteomics* 14, 2833-47 (2015)

the surface accessibility of the methionine sulfur was calculated for all possible surface methionine substitutions, The top 95 most accessible sites to methionine were mutated to methionine and each individual mutant was expressed in the aGFP Fab without mutating the three intrinsic and unreactive buried methionines. Remarkably, of those 95 sites, 93 methionine mutants expressed with high yield in *E. coli* (3-18 mg/L). All 93 retained high binding affinity for GFP, and 92 of those retained high thermostability as measured by differential scanning fluorimetry (DSF). When tested for labeling with 5 equivalents of the oxaziridine reagent (oxaziridine 1) for 2 hours, 57 mutants labeled to greater than 90%. This could potentially be improved with higher equivalents of oxaziridine. All mutants labeled stoichiometrically and specifically at the mutated methionine residue, as determined by whole protein mass spectrometry.

The suitability of the methionine substitutions for longer term in vivo applications was assessed. Of the 57 highly labeled sites, 12 representative sites were chosen to test conjugation stability as a function of location and temperature. The 12 candidate sites spanned both the heavy and light chain, as well as the variable and constant domains of the Fab arm. Each methionine-oxaziridine conjugate was incubated at 4° C., 25° C., and 37° C. for 3 days and the remaining conjugate was measured by whole protein MS. A strong temperature dependence was found for hydrolysis from 4° C., 25° C., and 37° C. There was considerable variation among the sites, but all sites had less than 60% remaining conjugate after 3 days at 37° C. The product had a +16 mass shift consistent with hydrolysis of the sulfimide to a sulfoxide product, which has also been previously reported. Since ADCs can have circulation times up to weeks in the body, it is preferable that the linkage is stable for an extended period of time at biological temperatures to retain ADC potency and to eliminate off-target toxicity due to free drug release.

Enhancing stability of oxaziridine conjugates. Two approaches were used to improve conjugation stability: (1) testing of different substituted oxaziridine analogs to improve linkage stability and (2) testing of more buried sites on the Fab scaffold that were hypothesized could better shield the sulfimide from hydrolysis. Fifteen different oxaziridine molecules were used, with various functionalities appended to the urea group, to determine if the resulting sulfimide bond could be further stabilized. One representative site, LC.T20M, was chosen that showed moderate stability at 37° C. for oxaziridine 1. All compounds were conjugated to LC.T20M site on the model aGFP Fab and stability of the sulfimide linkage was measured at 37° C. over 3 days. There was considerable variation in stability from 40-90% retained; nonetheless, two of oxaziridines (compound 5 and 8) provided stability over 80%. In a recent parallel study, it was shown that conjugate stability to isolated methionine was related to the electron density around the carbonyl as measured by the carbonyl stretching frequency. Indeed, a strong inverse correlation was observed between carbonyl stretching frequency and the measured stabilities on the Fab, as was also seen with isolated methionine. A new azide containing oxaziridine derivative (oxaziridine composition #16, Table 1) was synthesized, based on the more stable piperidine-derived oxaziridine composition #8, to enable copper-free click chemistry for ADC conjugation.

Next, it was investigated how lowering site accessibility may shield the resulting sulfimide linkage from hydrolysis. It was known that fully buried sites are unreactive. Therefore, 23 sites were chosen that had intermediate degrees of accessibility most of which were located on structured b-sheet regions. Remarkably, 19 of the 23 single methionine substitutions at these partially buried sites expressed at high levels in *E. coli* (3-50 mg/L); 18 retained high affinity to GFP, and 17 retained high thermostability. These less accessible sites were also less reactive, and thus the labeling reaction was increased to 20 equivalents of oxaziridine to better drive the reactivity. Four mutants that had greater than 85% stability were found when labeled with the oxaziridine azide composition #8 and incubated at 37° C. for 3 days. There was a slight inverse correlation between site accessibility and long-term stability but the lack of a strong correlation suggests that additional factors are at play besides simple site accessibility. Overall, it was found that the combination of selected oxaziridine derivatives and different site accessibility produced highly stable conjugates that were good candidates for ADC production.

Next, these mutations were incorporated into a trastuzumab Fab the ADC conjugates were texted for killing of breast cancer cell lines. However, it was observed that the wild-type trastuzumab Fab labeled 25% with the oxaziridine reagent when reacted at 20 equivalents, which was a desirable concentration of oxaziridine to label the less accessible sites. It was hypothesized that this additional and undesirable labeling was due to labeling of the methionine at position HC.M107 in the CDR H3 of trastuzumab. Simply mutating HC.M107 to an unreactive leucine eliminated labeling at this site. Furthermore, the HC.M107L mutation did not affect binding to HER2 on SKBR3 cells.

Two of the most stable sites, LC.R66M and LC.T74M, were chosen and incorporated methionine into the corresponding sites on trastuzumab aHER2 Fab antibody to use in cellular toxicity and serum stability assays. Both labeled to greater than 80% when reacted with 20 equivalents of oxaziridine composition #16. The two stable sites were individually converted to methionines on the trastuzumab Fab scaffold and then labeled with oxaziridine composition #16, followed by strain promoted click chemistry with DBCO-PEG4-valine-citrulline-MMAF to be used in a cellular toxicity assay. The cathepsin B cleavable linker valine-citrulline was chosen for its improved effect over a tested non-cleavable linker. The microtubule inhibitor MMAF was selected as the toxic payload due to its previously characterized strong potency in ADC formats and improved solubility compared to MMAE. Both ADCs showed high potency in a HER2-positive breast cancer cell line, BT474-M1, compared to either trastuzumab alone or an aGFP Fab control. The ADC conjugates were 10-100-fold more potent than the free MMAF reflecting their capacity as a drug chaperone. Interestingly, the ADC derived from the LC.R66M was about less active than LC.T74M due to a modest loss in affinity when conjugated with drug. However, upon conversion to a full IgG, the loss in affinity was greatly restored due to the higher avidity of the IgG and much lower off-rates. Both sites were also tested for their stability in human serum and showed similar levels compared to their stability measured in buffer. Thus, the two sites in the Fab arms are promising candidates for ADC formation.

Labeling and stability at homologous sites on the Fc domain. To explore more flexibility in labeling sites for methionine antibody conjugates, suitable labeling sites were probed on the Fc domain of the IgG. However, two endogenous methionines on the Fc (HC.M252 and HC.M428) that are surface exposed and one of which readily reacts with the oxaziridine. Also, it is known that these methionines sit directly at the FcRn binding site and that even oxidation at these sites can disrupt FcRn binding. It was found that labeling these methionines with oxaziridine ablated FcRn binding. In order to preserve FcRn binding, it was chosen to avoid conjugating at these sites. These methionines were scrubbed by mutation to leucine and it was found that these had little to no effect on overall protein stability or FcRn binding ability. An N297G mutation was also incorporated to prevent glycosylation of the Fc to simplify the mass spectrometry analysis. This triple Fc mutant was used as a template to search for more stable methionine conjugation sites.

To simplify the quest for new methionine sites in the Fc, the high structural similarity between the Fc and Fab arms was utilized. PyMol was used to align the five most stable conjugation sites from the Fab arm studies above to sites in the Fc domain. Single methionine mutants were introduced into identified sites in the native methionine-scrubbed Fc, expressed the variants in Expi293 mammalian cells, and these were tested for their labeling efficiency and stability. Interestingly, two of the engineered sites (HC.T307M, HC.T437M) did not label at all and thus could not be tested for their stability. The other three sites labelled to over 50%, and site HC.V262M showed greater than 80% labeling efficiency with virtually no hydrolysis after a three day incubation at 37° C.

Functional activity of methionine oxaziridine ADCs on breast cancer cell lines and in vivo efficacy in a breast cancer xenograft model. It was next tested how each of the three stables sites (LC.R66M, LC.T74M, and HC.V262M) performed as ADCs in an IgG format on HER2-positive breast cancer cell lines. On both SKBR3 and BT474-M1 cell lines, all three sites were almost equally effective at reducing cell growth (IC50~100-1000 pM). All three were 20-50-fold more potent than trastuzumab alone. When compared to one of the previously reported optimal engineered cysteine sites LC.V205C[20], comparable cell killing was observed at sites LC.T74M and HC.V262M. It was also tested how these conjugates performed by size exclusion chromatography (SEC) as a test for antibody aggregates and a proxy for good pharmacokinetics. ADCs produced at sites LC.T74M and HC.V262M showed a single symmetrical elution peaks comparable to trastuzumab, while site LC.R66M formed three broad peaks. It was also discovered that after reintroducing the wildtype N297 residue and thus glycosylation, labeling at site HC.V262M was not effective. It was hypothesized that this was because the glycans sit in the same pocket that the conjugated residue would occupy and thus the glycans prevent labeling. LC.T74M was nominated as a candidate for in vivo studies. Trastuzumab IgG was conjugated to valine-citrulline cleavable MMAF and a dose-response study was performed in a mouse xenograft BT474-M1 breast cancer model. A dose-response efficacy was observed and at the highest dose of 6 mg/kg inhibition of tumor growth compared to control across 5 weeks. At 6 mg/kg we increased efficacy was seen compared to trastuzumab alone, where one mouse did not respond at all to trastuzumab compared to all three mice responding to the ADC.

Discussion A systematic and general approach for identifying efficient, stoichiometric, and stable methionine labeling sites for antibodies using ReACT that preserves antibody function and stability for ADC applications was tested. A number of variables were explored and potential pitfalls were addressed to find optimal labeling sites. Surprisingly, almost all of the single methionine mutants were tolerated in the context of the trastuzumab scaffold. Of the 95 highly accessible methionine sites, 93 were expressed at wild-type levels and 92 retained a Tm greater than 77° C. Even for the 23 partially buried sites, 19 were expressed at wild-type levels and 17 maintained a high Tm. Methionine oxidation was not observed for the purified recombinant antibodies expressed either as Fabs in *E. coli* or as IgGs expressed from mammalian cells. This obviated the need to chemically reduce prior to conjugation with oxaziridine. This is a substantial advantage to cysteine labeling which typically requires reduction and reoxidation prior to thiol-conjugation. The conjugation to the oxaziridine was done rapidly (30 min at 5-30 fold excess) at room temperature in aqueous conditions and consistently produced high yields of the bioconjugate. For example, of the 92 accessible methionine sites expressed, 57 were labelled over 90%. Even for the 23 expressible partially buried methionine sites, 11 were labeled to over 80%.

The results demonstrated that endogenous methionines can be managed for antibody conjugations. In the aGFP trastuzumab Fab there are three buried methionines and these were unreactive and thus preserved them throughout the experiments. Upon switching to the wild type trastuzumab there was a reactive methionine in CDR H3. This was replaced with a leucine and did not affect the affinity of the antibody. Moreover, methionines are routinely mutated out of CDRs in therapeutic antibodies to avoid oxidation upon long-term storage or treatment. Two endogenous methionines in the Fc were readily mutated to leucine without significant impact on expression or binding.

Structure-activity analysis identified new oxaziridine compounds with significantly improved stability to hydrolysis. The stability tracked with the electron density surrounding the carbonyl as found in parallel studies on isolated methionine.

Significant variation in stability was observed depending on the site of modification. There is an inverse trend between accessibility and site stability. This may be because the sulfimide is shielded from water and hindered from being hydrolyzed. The hydrolysis reaction of the sulfimide is expected to go through a tetrasubstituted intermediate and neighboring sites will likely impact the stability of this intermediate based on the chemical environment.

These results demonstrate that site-specific modification of methionine by ReACT has great potential for antibody and protein bioconjugations. The expression of the methionine mutants was robust and the general tolerability of methionine mutations suggests multiple methionines could easily be introduced. The conjugation procedure is rapid, simple, and does not require pre-reduction. There is good flexibility with site selection and the resulting linkage can be stable at biological temperatures. The sites described here enable the selection of equivalent residues in other antibody scaffolds. For example, the discovery of the stable Fc site did not require a complete methionine surface scan, but rather simple homology modeling was sufficient to identify useful sites. Site-specific methionine labeling by ReACT offers more homogeneity of modification compared to lysine modification. It produced conjugates as stable as cysteine-maleimide conjugations, and robust ADC activity in a BT474-M1 mouse xenograft model. The methods demonstrated herein will be useful for many other antibody and protein bioconjugation applications such as for fluorescence, affinity labels, DNA barcoding, and protein-protein bioconjugation.

Methods. Selection of accessible conjugation sites. To estimate the relative solvent accessibility (RSA) of engineered methionines on a Fab, a computational methionine scan was performed with MODELLER using PDB structure 1FVE as a template. MODELLER generates homology models for comparative structure analysis by satisfaction of spatial restraints. Single methionine mutations were systematically modeled across the entire structure of the Fab including an additional model with a methionine appended at the end of the light chain for a total of 439 individual models generated. The solvent accessible surface area (SASA) of the engineered methionine sulfur atom was determined using the "get_area" function (dot solvent=1, dot_density=4, solvent_radius=1.4) in PyMol. Due to the stochasticity of the S-methyl group placement, the group was removed prior to SASA calculations and was found to reduce variability. The RSA was calculated by taking the SASA values and dividing by the maximum SASA value observed in the set. Positions were rank ordered and the top 95 sites with the highest RSA (excluding CDR positions, prolines and cysteines) were selected for bioconjugation.

Preparation and characterization of aGFP Fab methionine mutants. All methionine mutants were made using QUIKCHANGE™ (Agilent Technologies) to introduce single codon mutations onto the aGFP Fab. Fabs were expressed and purified by an optimized auto-induction protocol previously described in Hornsby et al. In brief, C43 (DE3) Pro +*E. coli* containing expression plasmids were grown in TB auto-induction media at 37° C. for 6 hours, then cooled to 30° C. for 16-18 hr. Cells were harvested by centrifugation and Fabs were purified by affinity chromatography. Fab purity and integrity was assessed by SDS-PAGE and intact protein mass spectrometry using a mass spectrometer and column (2.1 mm inner diameter, 50 mm length, 300 Å pore size, 1.7 μm particle size) connected to a liquid chromatography system. Deconvolution of mass spectra was performed using the maximum entropy algorithm.

Labeling of aGFP Fab methionine mutants with oxaziridine and Sulfo-DBCO-NHS. Fabs were prepared at 30 uM in PBS and labeled with 5 equivalents of the original oxaziridine azide reagent. The reaction proceeded for 2 hours at room temperature before being quenched with 500 mM methionine. Sulfo-DBCO-NHS was added at a final concentration of 625 uM and incubated at room temperature. Labeling was analyzed by intact protein mass spectrometry using a mass spectrometer.

Single-point kinetic screen. To determine if binding was perturbed by conjugation, a single-point kinetic screen was performed by bio-layer interferometry. Biotinylated-GFP was captured by streptavidin biosensors and the remaining biotin binding sites were saturated with free biotin. Association of 10 nM unlabeled or labeled Fab was measured for 15 min followed by dissociation for 30 min. $K_D$ values of all unlabeled and labelled Fabs were estimated to be sub-0.5 nM. Binding affinity for FcRn was performed in a similar manner but at pH 6.0 to mimic binding in the acidic endosome. Biotinylated FcRn was used as the loading ligand.

Protein stability Differential Scanning Fluorimetry (DSF) assay. Stability was measured by a DSF assay. In brief, Fabs (2 M) were incubated with protein gel stain in PBS. Fluorescence scanning was performed from 25° C.-95° C. at a rate of 1° C./min. Melting temperatures were calculated from the inflection point in the first-derivative curve.

Synthesis of Compounds. All oxaziridines compounds were previously synthesized and reported in Christian et al. A Physical Organic Approach to Tuning Reagents for Selective and Stable Methionine Bioconjugation. *ChemRxiv* (2019).

Parameter Derivation. A conformational search on the respective ureas and carbamates was performed using modeling suite without solvent corrections. A Monte-Carlo molecular mechanics method was employed. The output was restricted to structures within 1.30 kcal/mol (5 kJ/mol) of the lowest energy conformer. Conformers were submitted to a geometry optimization in Gaussian 09 using the def2-TZVP basis set and M06-2× functional. A triple zeta potential basis set was chosen along with the M06-2× functional, as these generally lead to quantitative correlations. Using a cutoff limit of 2.5 kcal/mol, the parameters of each low energy conformer were weighted using the Boltzmann distribution where the energy of a given conformer is calculated relative to the lowest energy conformation.

PyMol homology alignment. To determine analogous stable sites on the Fc, the alignment function was used in PyMol, using the PDB structure 1FVE (Fab) and 1H3X (Fc). Stable sites on light chain or heavy chain were aligned to either the CH2 or CH3 domains in the Fc. Corresponding positions were chosen on the Fc to mutate to methionine.

Expression of IgG single methionine mutants. IgGs containing the engineered methionines were expressed and purified from Hek293 cells. Briefly, 30 g of vector was transiently transfected into 75 million Hek293 cells. Cells were incubated for a total of 6 days at 37° C. in a 5% $CO_2$ environment before the supernatants were harvested by centrifugation. Protein was purified by affinity chromatography and assessed for quality and integrity by SDS-PAGE.

Conjugation of engineered methionine Fabs and IgGs with oxaziridine and DBCO-PEG4-valcit-MMAF. For Fab ADCs, endotoxins were removed prior to conjugation using endotoxin removal kits. For conjugation, Fabs were incubated at 50 M with 15 molar equivalents of compound 8 azide oxaziridine for 30 minutes at room temperature in PBS. For IgGs, IgGs were incubated at 10 M with 30 molar equivalents of compound 8 azide oxaziridine per methionine for 1 hour at room temperature in PBS. For both, the reaction was quenched by the addition of methionine and antibody was buffered exchanged into PBS using a desalting column. Then 10 molar equivalents of DBCO-PEG4-valcit-MMAF was added and the click reaction proceeded overnight at room temperature. The conjugate was desalted twice using two 0.5 mL columns to remove excess unconjugated drug. Full conjugation was monitored by intact protein mass spectrometry.

Conjugation of engineered cysteine ADCs for comparison. Engineered cysteine conjugation was performed as previously reported in Sassoon and Blanc, Antibody-Drug Conjugate (ADC) Clinical Pipeline: A Review. in 1-27 (2013). doi:10.1007/978-1-62703-541-5_1. In brief, after purification of the LC.V205C mutant aHer2 IgG (see IgG expression), the IgG (10 M) was buffer exchanged into 50 mM Tris-HCl, pH 7.5, 2 mM EDTA. DTT was added at 40-fold molar excess and incubated at room temperature for 16 hours. Desalting into PBS proceeded with columns. DHAA was added in 15-fold molar excess to reoxidize the interchain disulfides for 3 hours at room temperature. Maleimide-valcit-MMAF (was added at 3-fold molar excess and conjugation was monitored by mass spectrometry. Excess drug was removed by two desalting columns.

ADC cell killing assay in vitro. Antibody drug conjugate cell killing assays were performed using an MTT modified assay to measure cell viability. In brief, 10000 BT474-M1 or SKBR3 cells were plated in each well of a 96-well plate on day 0. On day 1, Fab/IgG was added in a 10-fold dilution series. Cells were incubated for 120 hr at 37° C. under 5% $CO_2$. On day 6, 40 μL of 2.5 mg/mL of tetrazolium bromide was added to each well and incubated at 37° C. under 5% $CO_2$ for 4 hours. Following, 100 L of 10% SDS 0.01M HCl was added to lyse the cells to release the MTT product. After 4 hours, absorbance at 600 nm was quantified using a plate reader.

ADC study in mouse xenograft model in vivo. The xenograft was performed with 6-8 week old nude female mice (NCR, nu/nu) (n=3 per group). Prior to tumor cell engraftment, mice were implanted subcutaneously with estradiol pellet (0.36 mg, 60 day release). BT474-M1 xenografts were then established by bilateral subcutaneous injection into the right and left flanks of mice with BT474-M1 tumor cells ($5\times10^6$ cells in 100 μl of serum free medium mixed 1:1 with MATRIGEL™. When BT474-M1 xenografts reached average volume of 200 $mm^3$ (measured as width×width×length×0.52), mice were dosed intravenously weekly for 3 weeks with PBS, drug alone, antibody alone and ADCs. Tumor size and body weight were monitored biweekly for 5 weeks total.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. An antigen-binding composition comprising an antibody scaffold;
   - wherein the antibody scaffold comprises complementarity determining region sequences (CDRs) set forth in SEQ ID NOs: 2-4 and 6-8, with the provision that the methionine of SEQ ID NO: 8 is substituted with leucine;
   - wherein the antibody scaffold comprises one or more introduced methionine residues present at a site in the antibody scaffold corresponding to LC066, LC074, and/or HC262; and
   - wherein a functional molecule is conjugated to each of the one or more introduced methionine residues.
2. The antigen-binding composition of claim 1, wherein the antibody scaffold is a trastuzumab scaffold or antigen-binding fragment thereof.
3. The antigen-binding composition of claim 1, wherein the antibody scaffold comprises:
   - a polypeptide comprising at least 95% sequence identity to SEQ ID NO: 9; and
   - a polypeptide comprising at least 95% sequence identity to SEQ ID NO: 10.
4. The antigen-binding composition of claim 1, wherein the antigen-binding composition comprises a whole antibody, an immunoglobulin monomer, or an antigen-binding antibody fragment.
5. The antigen-binding composition of claim 1, wherein the antigen-binding composition comprises an Fc sequence.
6. The antigen-binding composition of claim 5, wherein the Fc sequence comprises one or more amino acid substitutions selected from the following:
   - the methionine corresponding to position 217 of SEQ ID NO: 10 (HC.M252) is substituted with a non-methionine amino acid;
   - the methionine corresponding to position 393 of SEQ ID NO: 10 (HC.M428) is substituted with a non-methionine amino acid; and
   - the glutamine corresponding to position 262 of SEQ ID NO: 10 (HC.N297) is substituted with a non-glutamine amino acid.

7. The antigen-binding composition of claim 6, wherein the Fc sequence comprises one or more amino acid substitutions selected from the following:

the methionine corresponding to position 217 of SEQ ID NO: 10 (HC.M252) is substituted with leucine;

the methionine corresponding to position 393 of SEQ ID NO: 10 (HC.M428) is substituted with leucine; and the glutamine corresponding to position 262 of SEQ ID NO: 10 (HC.N297) is substituted with glycine.

8. The antigen-binding composition of claim 1, wherein a methionine residue is introduced at a site in the antibody scaffold corresponding to SEQ ID NO: 9 residue 48 (LC066).

9. The antigen-binding composition of claim 1, wherein a methionine residue is introduced at a site in the antibody scaffold corresponding to SEQ ID NO: 9 residue 56 (LC074).

10. The antigen-binding composition of claim 1, wherein a methionine residue is introduced at a site in the antibody scaffold corresponding to SEQ ID NO: 10 residue 225 (HC262).

11. The antigen-binding composition of claim 1, wherein the functional molecule is conjugated to the one or more introduced methionine residues by oxaziridine-mediated conjugation.

12. The antigen-binding composition of claim 11, wherein the oxaziridine-mediated conjugation is achieved using an oxaziridine selected from the group consisting of

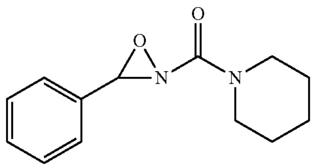
,
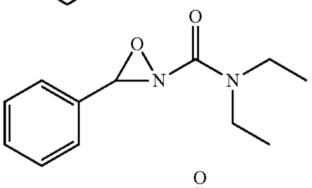
, and
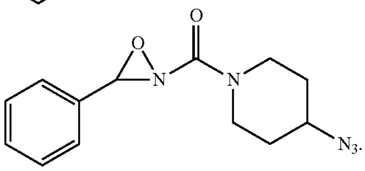
.

13. The antigen-binding composition of claim 1, wherein the functional molecule comprises a therapeutic agent.

14. The antigen-binding composition of claim 13, wherein the functional molecule comprises a cytotoxic agent.

15. The antigen-binding composition of claim 1, wherein the functional molecule comprises a detection agent.

16. A method of functionalizing a polypeptide comprising one or more methionine residues with a selected composition, comprising the steps of reacting the polypeptide with an oxaziridine composition comprising an oxaziridine selected from the group consisting of,

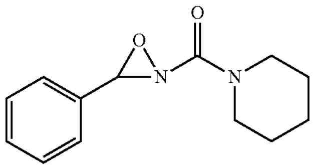
,
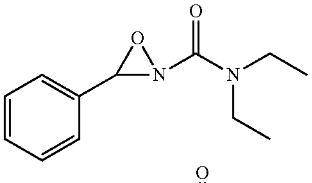
, and
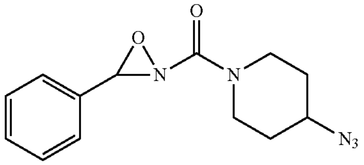

under suitable conditions for the formation of an intermediate composition comprising a sulfimide bond by the sulfur atom of the one or more introduced methionines; and performing a second reaction between the intermediate composition and the selected composition under suitable conditions for azide-alkyne reaction, wherein the selected composition comprises an alkyne group, thereby conjugating the selected composition to the polypeptide by sulfimide linkage.

17. The method of claim 16, wherein the polypeptide is integral to an antigen-binding composition comprising an antibody or antigen binding fragment thereof.

18. The method of claim 17, wherein the selected composition is a therapeutic agent or detection agent.

19. A reagent for oxaziridine-mediated conjugation of molecules, comprising

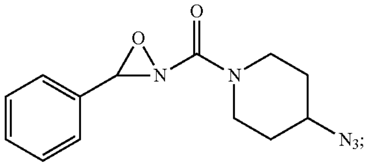 [SMILES: [N-]=[N+]=NC1CCN(C(=O)N2OC2c2ccccc2)CC1]
;

20. The antigen-binding composition of claim 9, further comprising a methionine residue introduced at a site in the antibody scaffold corresponding to SEQ ID NO: 9 residue 48 (LC066).

21. The antigen-binding composition of claim 9, further comprising a methionine residue introduced at a site in the antibody scaffold corresponding to SEQ ID NO: 10 residue 225 (HC262).

* * * * *